(12) United States Patent
Horgan et al.

(10) Patent No.: US 12,421,628 B2
(45) Date of Patent: Sep. 23, 2025

(54) MASSIVELY PARALLEL ENZYMATIC SYNTHESIS OF NUCLEIC ACID STRANDS

(71) Applicant: DNA Script, Le Kremlin-Bicêtre (FR)

(72) Inventors: Adrian Horgan, Le Kremlin-Bicêtre (FR); Xavier Godron, Le Kremlin-Bicêtre (FR); Thomas Ybert, Paris (FR); Robert Nicol, Le Kremlin-Bicêtre (FR)

(73) Assignee: DNA Script, Le Kremlin-Bicêtre (FR)

( * ) Notice: Subject to any disclaimer, the term of this patent is extended or adjusted under 35 U.S.C. 154(b) by 1226 days.

(21) Appl. No.: 17/259,839

(22) PCT Filed: Jul. 5, 2019

(86) PCT No.: PCT/EP2019/068183
§ 371 (c)(1),
(2) Date: Jan. 12, 2021

(87) PCT Pub. No.: WO2020/020608
PCT Pub. Date: Jan. 30, 2020

(65) Prior Publication Data
US 2021/0332351 A1    Oct. 28, 2021

(30) Foreign Application Priority Data
Jul. 23, 2018  (EP) .................................. 18306000

(51) Int. Cl.
C40B 50/06      (2006.01)
C12N 15/10      (2006.01)
G16B 50/00      (2019.01)

(52) U.S. Cl.
CPC .......... *C40B 50/06* (2013.01); *C12N 15/1068* (2013.01); *G16B 50/00* (2019.02)

(58) Field of Classification Search
None
See application file for complete search history.

(56) References Cited

U.S. PATENT DOCUMENTS 4,772,691 A    9/1988 Herman
5,047,524 A    9/1991 Andrus
(Continued)

FOREIGN PATENT DOCUMENTS

CN    1916630 A    2/2007
CN    107771223 A    3/2018
(Continued)

OTHER PUBLICATIONS

International Preliminary Report on Patentability for corresponding PCT Application No. PCT/EP2019/068183, dated Jan. 26, 2021, 7 pages.
(Continued)

*Primary Examiner* — Christian C Boesen
(74) *Attorney, Agent, or Firm* — Morrison & Foerster LLP

(57) ABSTRACT

The invention is directed to methods for massively parallel template-free enzymatic synthesis of a plurality of different polynucleotides of predetermined sequences. In one aspect, methods of the invention employ large scale arrays of reaction sites each associated with at least one working electrode for controlling deprotection and deblocking steps at predetermined user selected sites. In another aspect, the invention provides template-free enzymatic synthesis with proofreading, wherein completed polynucleotides at predetermined reaction sites are sequenced using a sequencing by synthesis technique, particularly employing electrochemically labile blocking groups.

6 Claims, 13 Drawing Sheets

Specification includes a Sequence Listing.

(56) References Cited

U.S. PATENT DOCUMENTS

| | | |
|---|---|---|
| 5,126,022 A | 6/1992 | Soane et al. |
| 5,262,530 A | 11/1993 | Andrus |
| 5,367,066 A | 11/1994 | Urdea et al. |
| 5,436,143 A | 7/1995 | Hyman |
| 5,472,672 A | 12/1995 | Brennan |
| 5,474,796 A | 12/1995 | Brennan |
| 5,498,392 A | 3/1996 | Wilding et al. |
| 5,516,664 A | 5/1996 | Hyman |
| 5,587,128 A | 12/1996 | Wilding et al. |
| 5,602,000 A | 2/1997 | Hyman |
| 5,656,745 A | 8/1997 | Bischofberger |
| 5,667,667 A | 9/1997 | Southern |
| 5,700,642 A | 12/1997 | Monforte et al. |
| 5,739,386 A | 4/1998 | Holmes |
| 5,744,595 A | 4/1998 | Srivastava |
| 5,763,594 A | 6/1998 | Hiatt et al. |
| 5,798,210 A | 8/1998 | Canard |
| 5,808,045 A | 9/1998 | Hiatt |
| 5,830,655 A | 11/1998 | Monforte et al. |
| 5,847,105 A | 12/1998 | Baldeschwieler |
| 5,858,195 A | 1/1999 | Ramsey |
| 5,872,244 A | 2/1999 | Hiatt |
| 5,917,031 A | 6/1999 | Miura |
| 5,925,732 A | 7/1999 | Ecker |
| 5,935,527 A | 8/1999 | Andrus |
| 5,990,300 A | 11/1999 | Hiatt |
| 6,001,229 A | 12/1999 | Ramsey |
| 6,010,607 A | 1/2000 | Ramsey |
| 6,015,880 A | 1/2000 | Baldeschwieler |
| 6,028,189 A | 2/2000 | Blanchard |
| 6,033,546 A | 3/2000 | Ramsey |
| 6,054,034 A | 4/2000 | Soane et al. |
| 6,093,302 A | 7/2000 | Montgomery |
| 6,187,164 B1 | 2/2001 | Warren |
| 6,214,987 B1 | 4/2001 | Hiatt |
| 6,232,465 B1 | 5/2001 | Hiatt |
| 6,251,595 B1 | 6/2001 | Gordon et al. |
| 6,280,595 B1 | 8/2001 | Montgomery |
| 6,306,599 B1 | 10/2001 | Perbost et al. |
| 6,323,043 B1 | 11/2001 | Caren et al. |
| 6,384,210 B1 | 5/2002 | Blanchard |
| 6,399,952 B1 | 6/2002 | Maher et al. |
| 6,419,883 B1 | 7/2002 | Blanchard |
| 6,426,184 B1 | 7/2002 | Gao |
| 6,444,111 B1 | 9/2002 | Montgomery |
| 6,613,525 B2 | 9/2003 | Nelson et al. |
| 6,623,929 B1 | 9/2003 | Densham |
| 6,664,079 B2 | 12/2003 | Ju |
| 6,777,189 B2 | 8/2004 | Wei |
| 6,921,636 B1 | 7/2005 | Brennan |
| 6,960,437 B2 | 11/2005 | Enzelberger et al. |
| 7,057,026 B2 | 6/2006 | Barnes et al. |
| 7,078,499 B2 | 7/2006 | Odedra |
| 7,125,671 B2 | 10/2006 | Sood |
| 7,223,541 B2 | 5/2007 | Fuller et al. |
| 7,270,951 B1 | 9/2007 | Stemple |
| 7,276,336 B1 | 10/2007 | Webb et al. |
| 7,345,159 B2 | 3/2008 | Ju |
| 7,407,757 B2 | 8/2008 | Brenner |
| 7,491,680 B2 | 2/2009 | Gao |
| 7,494,797 B2 | 2/2009 | Mueller |
| 7,534,561 B2 | 5/2009 | Sana et al. |
| 7,544,794 B1 | 6/2009 | Benner |
| 7,566,537 B2 | 7/2009 | Balasubramanian |
| 7,635,578 B2 | 12/2009 | Ju |
| 7,713,698 B2 | 5/2010 | Ju |
| 7,790,869 B2 | 9/2010 | Balasubramanian |
| 7,838,466 B2 | 11/2010 | Gao |
| 7,932,025 B2 | 4/2011 | Carr |
| 7,939,259 B2 | 5/2011 | Kokoris |
| 8,034,923 B1 | 10/2011 | Benner |
| 8,212,020 B2 | 7/2012 | Benner |
| 8,263,335 B2 | 9/2012 | Carr |
| 8,394,586 B2 | 3/2013 | Balasubramanian |
| 8,674,086 B2 | 3/2014 | Liu |
| 8,808,988 B2 | 8/2014 | Zhao |
| 8,808,989 B1 | 8/2014 | Efcavitch |
| 8,895,249 B2 | 11/2014 | Shen et al. |
| 9,075,041 B2 | 7/2015 | Kavusi et al. |
| 9,121,062 B2 | 9/2015 | Balasubramanian |
| 9,267,213 B1 | 2/2016 | Maurer et al. |
| 9,279,149 B2 | 3/2016 | Efcavitch |
| 9,339,782 B1 | 5/2016 | Gindilis |
| 9,388,463 B2 | 7/2016 | Balasubramanian |
| 9,410,197 B2 | 8/2016 | Bergmann |
| 9,476,080 B2 | 10/2016 | Li et al. |
| 9,695,470 B2 | 7/2017 | Efcavitch |
| 9,771,613 B2 | 9/2017 | Efcavitch |
| 9,810,688 B2 | 11/2017 | Fomina |
| 9,874,538 B2 | 1/2018 | Johnson et al. |
| 9,896,709 B2 | 2/2018 | Makarov |
| 9,910,008 B2 | 3/2018 | Johnson et al. |
| 9,928,869 B2 | 3/2018 | Church |
| 9,957,549 B2 | 5/2018 | Armour |
| 9,996,778 B2 | 6/2018 | Church |
| 10,011,549 B2 | 7/2018 | Johnson |
| 10,035,920 B2 | 7/2018 | Omenetto |
| 10,041,905 B2 | 8/2018 | Johnson |
| 10,379,080 B2 | 8/2019 | Johnson |
| 10,384,189 B2 | 8/2019 | Peck |
| 10,435,676 B2 | 10/2019 | Champion |
| 10,669,304 B2 | 6/2020 | Indermuhle |
| 10,683,536 B2 | 6/2020 | Efcavitch |
| 10,752,887 B2 | 8/2020 | Champion |
| 10,982,276 B2 | 4/2021 | Efcavitch |
| 2001/0018512 A1 | 8/2001 | Blanchard |
| 2003/0027219 A1 | 2/2003 | Ilsley |
| 2003/0170698 A1 | 9/2003 | Gascoyne et al. |
| 2003/0186226 A1 | 10/2003 | Brennan et al. |
| 2004/0106728 A1 | 6/2004 | McGall et al. |
| 2004/0238369 A1 | 12/2004 | Southern |
| 2005/0227316 A1 | 10/2005 | Santi |
| 2005/0243152 A1 | 11/2005 | Rosa |
| 2006/0054511 A1 | 3/2006 | Maurer |
| 2006/0102471 A1 | 5/2006 | Maurer |
| 2007/0034513 A1 | 2/2007 | Maurer |
| 2009/0093381 A1 | 4/2009 | Wang |
| 2009/0275086 A1 | 11/2009 | Gibson |
| 2010/0041041 A1 | 2/2010 | Litosh |
| 2011/0091870 A1 | 4/2011 | Lang |
| 2011/0171649 A1 | 7/2011 | Kutyavin |
| 2013/0341561 A1 | 12/2013 | Maurer |
| 2014/0363851 A1 | 12/2014 | Efcavitch |
| 2014/0363852 A1 | 12/2014 | Efcavitch |
| 2015/0344876 A1 | 12/2015 | Peterson |
| 2016/0040227 A1 | 2/2016 | Mir |
| 2016/0186166 A1* | 6/2016 | Poehmerer ........ B01L 3/502761 204/600 |
| 2017/0141793 A1 | 5/2017 | Strauss et al. |
| 2017/0260521 A1 | 9/2017 | Peterson |
| 2018/0016609 A1 | 1/2018 | Chen |
| 2018/0023108 A1 | 1/2018 | Chen |
| 2018/0201968 A1 | 7/2018 | Chen |
| 2018/0230509 A1 | 8/2018 | Chen et al. |
| 2018/0265921 A1 | 9/2018 | Chen et al. |
| 2018/0318834 A1 | 11/2018 | Fomina |
| 2019/0030149 A1 | 1/2019 | Li et al. |
| 2019/0040459 A1 | 2/2019 | Efcavitch |
| 2019/0062804 A1 | 2/2019 | Church |
| 2019/0078065 A1 | 3/2019 | Baiga et al. |
| 2019/0078126 A1 | 3/2019 | Baiga et al. |
| 2019/0144905 A1 | 5/2019 | Chen |
| 2019/0145013 A1 | 5/2019 | Kalhor |
| 2019/0264248 A1 | 8/2019 | Ybert |
| 2019/0300923 A1 | 10/2019 | Ybert |
| 2019/0338331 A1 | 11/2019 | Chen |
| 2020/0231619 A1 | 7/2020 | Ybert |

FOREIGN PATENT DOCUMENTS

| | | |
|---|---|---|
| EP | 1165786 B1 | 7/2008 |
| EP | 3067809 | 9/2016 |
| EP | 2876166 B1 | 12/2016 |
| WO | WO1991/06678 | 5/1991 |

(56) References Cited

FOREIGN PATENT DOCUMENTS

| WO | WO1995/25116 | 9/1995 |
|---|---|---|
| WO | WO1996/07669 | 3/1996 |
| WO | WO1998/41531 | 9/1998 |
| WO | 9919717 | 4/1999 |
| WO | 0224322 | 3/2002 |
| WO | WO2004/018497 | 3/2004 |
| WO | WO2005/059096 | 6/2005 |
| WO | 2008048222 A2 | 4/2008 |
| WO | 2010110775 A1 | 9/2010 |
| WO | 2010134992 | 11/2010 |
| WO | 2014014991 | 1/2014 |
| WO | 2014014991 A2 | 1/2014 |
| WO | WO2014/165864 | 10/2014 |
| WO | 2015159023 | 10/2015 |
| WO | WO2016/028802 | 2/2016 |
| WO | WO2016/034807 | 3/2016 |
| WO | 2016094512 | 6/2016 |
| WO | 2016094512 A1 | 6/2016 |
| WO | 2016139477 A1 | 9/2016 |
| WO | 2017009663 A1 | 1/2017 |
| WO | 2017011492 A1 | 1/2017 |
| WO | 2017176541 | 10/2017 |
| WO | 2017176541 A1 | 10/2017 |
| WO | 2017196783 | 11/2017 |
| WO | 2017196783 A1 | 11/2017 |
| WO | 2017216472 | 12/2017 |
| WO | 2018057526 A2 | 3/2018 |
| WO | 2018102554 A1 | 6/2018 |
| WO | WO2018/134616 | 7/2018 |
| WO | 2019030149 A1 | 2/2019 |
| WO | WO2019/075211 | 4/2019 |
| WO | WO2020/020608 | 1/2020 |
| WO | WO2020/043846 | 3/2020 |
| WO | WO2020/077227 | 4/2020 |
| WO | WO2020/099451 | 5/2020 |
| WO | WO2020/165137 | 8/2020 |
| WO | WO2020/165334 | 8/2020 |
| WO | 2020178604 A1 | 9/2020 |

OTHER PUBLICATIONS

Bai et al, "Study of the enzymatic activity change due to inkjet printing for biosensor fabrication," ACS Biomaterials Sci. Eng., 7(2): 787-793 (2021).
Bal et al, "Digital printing of enzymes on textile substrates as functional materials," J. Fiber Bioengineering and Informatics, 7(4): 595-602 (2014).
Beabealashvilli et al, "Nucleoside 5'-triphosphates modified at sugar residues as substrates for calf thymus terminal deoxynucleotidyl transferase and for AMV reverse transcriptase," Biochim. Biophys. Acta., 868(2-3): 136-144 (1986).
Becker et al, "The enzymatic cleavage of phosphate termini from polynucleotides," J. Biol. Chem., 242(5): 936-950 (1967).
Biswas et al, "Effects of ink characteristics and piezo-electric inkjetting parameters on lysozyme activity," Scientific Reports, 9: 18252 (2019).
Blanchard et al, "High-density oligonucleotide arrays," Biosensors & Bioelectronics, 11(6/7): 687-690 (1996).
Bornholt et al, "A DNA-based archival storage system," ASPLOS'16 (Apr. 2-6, 2016, Atlanta, GA, USA).
Burgold et al, "Evolution and operating experiences with different drop-on-demand systems," Macromolecular Rapid Communications, 26: 265-280 (2005).
Calvert, "Inkjet printing for materials and devices," Chem. Mater., 13: 3299-3305 (2001).
Cameron et al, "3'-phosphatase activity in T4 polynucleotide kinase," Biochemistry, 16(23): 5120-5126 (1977).
Canard et al, "DNA polymerase fluorescent substrates with reversible 3'-tags," Gene, 148: 1-6 (1994).
Canard et al, "Catalytic editing properties of DNA polymerases," Proc. Natl. Acad. Sci., 92: 10859-10863 (1995).

Chang et al, "Molecular biology of terminal transferase," CRC Critical Reviews in Biochemistry, 21(1): 27-52 (1986).
Chen et al, "The history and advances of reversible terminators used in new generations of sequencing technology," Genomics Proteomics Bioinformatics, 11: 34-40 (2013).
Choi et al, "Inkjet-based multilayered growth factor-releasing nanofilms for enhancing proliferation of mesenchymal stem cells in vitro," J. Industrial and Engineering Chemistry, 50: 36-40 (2017).
Chrisey et al, "Fabrication of patterned DNA surfaces," Nucleic Acids Research, 24(15): 3040-3047 (1996).
Cook et al, "Inkjet delivery of glucose oxide," Chemical Communications, 46: 5452-5454 (2010).
Cox, "Long-term data storage in DNA," Trends in Biotechnology, 19(7): 247-250 (2001).
Delaney et al, "Injet printing of proteins," Soft Matter, 5: 4866-4877 (2009).
Delarue et al, "Crystal structures of a template-independent DNA polymerase: murine terminal deoxynucleotidyltransferase," EMBO J., 21(3): 427-439 (2002).
Delehanty et al, "A microarray immunoassay for simultaneous detection of proteins and bacteria," Anal. Chem., 74(21): 5681-5687 (2002).
Delehanty et al, "Method for printing functional protein arrays," Biotechniques, 34(2): 380-385 (2003).
Derby, "Bioprinting: inkjet printing proteins and hybrid cell-containing materials and structures," J. Materials Chemistry, 18: 57617-5721 (2008).
Derby, "Inkjet printing of functional and structural materials: fluid property requirements, feature stability, and resolution," Annual Reviews Materials Research, 40: 395-414 (2010).
DeSilva et al, "New trends of digital data storage in DNA," BioMed Research International, 2016: article ID 8072463, 14 pages.
Dong et al, "An experimental study of drop-on-demand drop formation," Physics of Fluids, 18: 072102 (2006).
Egeland et al, "An electrochemical redox couple activated by microelectrodes for confined chemical patterning of surfaces," Anal. Chem., 74: 1590-1596 (2002).
Ferrero et al, "Chemoenzymatic transformations in nucleoside chemistry," Monatshefte fur Chemie, 131: 585-616 (2000).
Fixe et al, "Thin film micro arrays with immobilized DNA for hybridization analysis," Mat. Res. Soc. Symp. Proc., vol. 723 (2002).
Flickinger et al, "Differential incorporation of biotinylated nucleotides by terminal deoxynucleotidyl transferase," Nucleic Acids Research, 20(9): 2382 (1992).
Galliker et al, "Open-atmosphere sustenance of highly volatile attoliter-size droplets on surfaces," Proc. Natl. Acad. Sci., 110(33): 13255-13260 (2013).
Gans et al, "Inkjet printing of polymer micro-arrays and libraries: instrumentation, requirements, and perspectives," Macromol. Rapid Commun., 24: 659-666 (2003).
Gao et al., "In situ synthesis of oligonucleotide microarrays," Biopolymers, 73: 579-596 (2004).
Gao et al, "A flexible light-directed DNA chip synthesis gated by deprotection using solution photogenerated acids," Nucleic Acids Research, 29(22): 4744-4750 (2001).
Gates et al, "Endonuclease V of *Escherichia coli*," J. Biol. Chem., 252(5): 1647-1653 (1977).
Gebeyehu et al, "Novel biotinylated nucleotide—analogs for labeling and colorimetric detection of DNA," Nucleic Acids Research, 15(11): 4513-4534 (1987).
Gdor et al, "Multienzyme inkjet printied 2D arrays," Chem. Comm., 46: 5452-5454 (2015).
Gillam et al, "Enzymatic synthesis of deoxyribo-oligonucleotides of defined sequence. Deoxyribo-oligonucleotide synthesis," Nucleic Acids Research, 1(12): 1649-1664 (1974).
Gopinath et al, "Optimized assembly and covalent coupling of single-molecule DNA origami nanoarrays," ACS Nano, 8(12): 12030-12040 (2014).
Heinze, "Ultramicroelectrodes in electrochemistry," Angew. Chem. Int. Ed. Engl., 32: 1268-1288 (1993).

(56) References Cited

OTHER PUBLICATIONS

Huang et al, "Multiple cleavage activities of endonuclease V from Thermotoga maritima: recognition and strand nicking mechanism," Biochemistry, 40: 8738-8748 (2001).
Hughes et al, "Expression profiling using microarrays fabricated by an ink-jet oligonucleotide synthesizer," Nature Biotechnology, 19: 342-347 (2001).
Hutter et al, "Labeled nucleoside triphosphates with reversibly terminating aminoalkoxyl groups," Nucleosides, Nucleotides & Nucleic Acids, 29(11): 879-895 (2010).
Ihalainen et al, "Printing technologies for biomolecule and cell-based applications," International Journal of Pharmaceutics, 494(2): 585-592 (2015).
IPR2013-00128 re U.S. Pat. No. 7,057,026 Final Written Decision (Jul. 25, 2014).
IPR2013-00266 re U.S. Pat. No. 8,158,346 Final Written Decision (Oct. 28, 2014).
IPR2017-02172 re U.S. Pat. No. 7,566,537 Decision (Apr. 20, 2018).
Jang et al, "Influence of fluid physical properties on ink-jet printability," Langmuir, 25:2629-2635 (2009).
Kawczynski et al, "Electrochemical reduction of azido nucleosides: Mechanism and synthetic and analytical applications," Bioelectrochemistry and Bioenergetics, 26(3): 441-452 (1991).
Kawczynski et al, "Electrochemical reduction products of azido nucleosides, including Zidovudine (AZT): mechanisms and relevance to their intracellular metabolism," Acta Biochimica Polonica, 40(2): 213-223 (1993).
Kim et al, "Electrochemical deprotection for site-selective immobilization of biomolecules," Langmuir, 18: 1460-1462 (2002).
Knapp et al, "Fluoride-Cleavable, Fluorescently Labelled Reversible Terminators: Synthesis and Use in Primer Extension," Chem. Eur. J., 17: 2903-2915 (2011).
Kobayashi et al, "A microfluidic device for conducting gas-liquid-solid hydrogenation reactions," Science, 304: 1305-1308 (2004).
Kore et al, "Synthesis and activity of modified cytidine 5'-monophosphate probes for T4 RNA ligase 1," Nucleosides Nucleotides Nucleic Acids, 28(4): 292-302 (2009).
Lausted et al, "POSaM: a fast, flexible open-source, inkjet oligonucleotide synthesizer and microarrayer," Genome Biology, 5:R58 (2004).
Le, "Progress and trends in ink-jet printing technology," Recent Progress in Ink Jet Technologies II, chapter 1 (1999).
Lee et al, "Enzymatic DNA synthesis for digital information storage," bioRxiv, http://dx.doi.org/10.1101/348987 (Jun. 16, 2018).
Lee et al, "Terminator-free template independent enzymatic DNA synthesis for digital information storage," Nature Comm., 10: 2383 (2019).
Lee et al, "Direct on-paper inkjet printing of kinase-to-kinase phosphorylation cascade reactions," ACS Omega, 4: 7866-7873 (2019).
Lee et al, "Inkjet-printing inhibitory assay based on determination of ejection volume," Anal. Chem. 89(3): 2009-2016 (2016).
Lee et al, "Endonuclease V-mediated deoxyinosine excision repair in vitro," DNA Repair, 9: 1073-1079 (2010).
Lemmo et al, "Characterization of an inkjet chemical microdispenser for combinatorial library synthesis," Anal. Chem., 69: 543-551 (1997).
Li et al, "A photocleavable fluorescent nucleotide for DNA sequencing and analysis," Proc. Natl. Acad. Sci., 100(2): 414-419 (2003).
Li et al, "An oligonucleotide synthesizer based on a microreactor chip and an inkjet printer," Scientific Reports, 9: 5058 (2019).
Lin et al, "Recent patents and advances in the next-generation sequencing technologies," Recent Patents in Biomedical Engineering, 2008(1): 60-67 (2008).
Lonini et al, "Dispensing an enzyme-conjugated solution into an ELISA plate by adapting ink-jet printers," Journal of Biochemical and Biophysical Methods, 70(6): 1180-1184 (2008).
Mackey et al, "New approach to the synthesis of polyribonucleotides of defined sequence," Nature, 233: 551-553 (1971).
Mairanovsky, "Electro-deprotection-electrochemical removal of protecting groups," Angew-Chem-Int-Ed-Engl, 15(5): 281-292 (1976).
Mi et al, "Dissecting endonuclease and exonuclease activities in endonuclease V from Thermotoga maritime," Nucleic Acids Research, 39(2): 536-544 (2011).
Michelson et al, "Characterization of the homopolymer tailing reaction catalyzed by terminal deoxynucleotidyl transferase," J. Biol. Chem., 257(24): 14773-14782 (1982).
Miyahara et al, "Fabrication of microtemplates for the control of bacterial immobilization," J. Vac. Sci. Technol. A 27(5):1183-1187 (2009).
Montenegro, "The electrochemical cleavage of protecting groups," Electrochimica Acta, 31(6): 607-620 (1986).
Montenegro-Nicolini et al, "Inkjet printing of proteins: an experimental approach," AAPS Journal, 19(1): 234-243 (2016).
Morse et al, "Detection of inosine in messenger RNA by inosine-specific cleavage," Biochemistry, 36(28): (Jul. 15, 1997).
Motea et al, "Terminal deoxynucleotidyl transferase: The story of a misguided DNA polymerase," Biochim Biophys Acta, 1804(5): 1151-1166 (2010).
Neugebauer et al, "Analysis in ultrasmall volumes: microdispensing of picoliter droplets and analysis without protection from evaporation," Anal. Chem., 76: 458-463 (2004).
Nishioka et al, "Protein damage in drop-on-demand printers," J. Am. Chem. Soc., 126: 16320-16321 (2004).
Olejnik et al, "Photocleavable biotin derivatives: A versatile approach for the isolation of biomolecules," Proc. Natl. Acad. Sci., 92: 7590-7594 (1995).
Palla et al, "DNA sequencing by synthesis using 3'-O-azidomethyl nucleotide reversible terminators and surface-enhanced Raman spectroscopic detection," RSC Adv. 4: 49342 (2014).
Petrie et al, "A novel biotinylated adenylate analogue derived from pyrazolo[3,4-d] pyrimidine for labeling DNA probes," Bioconjug. Chem., 2(6): 441-446 (1991).
Rasolonjatovo et al, "Development of a new sequencing method: 3'-ester cleavage catalyzed by Taq DNA polymerase," Nucleosides & Nucleotides, 18(4&5): 1021-1022 (1999).
Roth et al, "CombiMatrix CustomArray 12K and eC reader: a flexible platform for highly parallel electrochemical evaluation of enzyme activity," 209th ECS Meeting, Abstract #561 (2006).
Schott et al, "Single-step elongation of oligodeoxynucleotides using terminal deoxynucleotidyl transferase," Eur. J. Biochem., 143: 613-620 (1984).
Serafinowski et al, "Novel photoacid generators for photodirected oligonucleotide synthesis," J. Am. Chem. Soc., 125: 962-965 (2003).
Tekin et al, "Inkjet printing as a deposition and patterning tool for polymers and inorganic particles," Soft Matter, 4: 703-713 (2008).
Thomas et al, "Effects of shear on proteins in solution," Biotechnology Letters, 33(3): 443-456 (2010).
Ud-Dean, "A theoretical model for template-free synthesis of long DNA sequence," Syst. Synth. Biol., 2: 67-73 (2008).
Uemura et al, "Regioselective deprotection of 3', 5'-O-acylated pyrimidine nucleosides by lipase and esterase," Tetrahedron Lett., 30(29): 3819-3820 (1989).
Ulijn et al, "Protease-catalyzed peptide synthesis on solid support," J. Am. Chem. Soc., 124: 10988-10989 (2002).
Vik et al, "Endonuclease V cleaves at inosine in RNA," Nature Communications, 4: article No. 2271 (2013).
Wu et al, "3'-O-modified nucleotides as reversible terminators for pyrosequencing," Proc. Natl. Acad. Sci., 104(42): 16462-16467, (2007).
Wu, Thesis, "Molecular engineering of novel nucleotide analogues for DNA sequencing by synthesis," Columbia University, total 232 pages, (2008).
Yao et al, "Purification and characterization of a novel deoxyinosine-specific enzyme, deoxyinosine 3' endonuclease, from *Escherichia coli*," J. Biol. Chem., 269(23): 16260-16268 (1994).
Yao et al, "Interaction of deoxyinosine 3'-endonuclease from *Escherichia coli* with DNA containing deoxyinosine," J. Biol. Chem., 270 (48): 28609-28616 (1995).
Yao et al, "Further characterization of *Escherichia coli* Endonuclease V," J. Biol. Chem. 272(49): 30774-30779 (1997).

(56) References Cited

OTHER PUBLICATIONS

Yudin et al, "Combinatorial electrochemistry," Current Opinion in Chemical Biology, 5: 269-272 (2001).
Zavgorodny et al, "1-Alkylthioalkylation of nucleoside hydroxyl functions and its synthetic applications: A new versatile method in nucleoside chemistry," Tetrahedron Lett., 32(51): 7593-7596 (1991).
Written Opinion dated Mar. 10, 2016 for PCT/FR2015/052310, 17 pages.
Search Report and Written Opinion dated May 29, 2020 for PCT/EP2020/053417, 11 pages.
Beaucage et al. (1992) "Advances in the Synthesis of Oligonucleotides by the Phosphoramidite Approach" Tetrahedron, 48(12): 2223-2311.
Bentley et al. (2008) "Accurate whole human genome sequencing using reversible terminator chemistry" Nature, 456: 53-59.
Bornholt et al. (2017) "Toward a Dna-Based Archival Storage System" IEEE Micro, 37(3): 98-104.
Church et al. (2012) "Next-Generation Digital Information Storage in DNA" Science, 337(6102): 1628.
Egeland et al. (2005) "Electrochemically directed synthesis of oligonucleotides for DNA microarray fabrication" Nucleic Acids Research, 33(14): e125.
Fomina et al. (2016) "An electrochemical platform for localized pH control on demand" LabChip, 16: 2236-2244.
Goldman et al. (2013) "Toward practical high-capacity low-maintenance storage of digital information in synthesised DNA" Nature, 494: 77-80.
Greenberg et al. (1994) "Cleavage of Oligonucleotides from Solid-Phase Supports Using o-Nitrobenzyl Photochemistry" J. Org. Chem. 59:746-753.
Guo et al (2008) "Four-color DNA sequencing with 3'-O-modified nucleotide reversible terminators and chemically cleavable fluorescent dideoxynucleotides" Proc. Natl. Acad. Sci., 105(27): 9145-9150.
Guo et al (2010) "An Integrated System for DNA Sequencing by Synthesis Using Novel Nucleotide Analogues" Acc. Chem. Res. 43(4): 551-563.
Holmes et al. (1997) "Model Studies for New o-Nitrobenzyl Photolabile Linkers: Substituent Effects on the Rates of Photochemical Cleavage" J. Org. Chem. 62(8): 2370-2380.
Jensen et al. (2018) "Template-Independent Enzymatic Oligonucleotide Synthesis (TiEOS): Its History, Prospects, and Challenges" Biochemistry, 57: 1821-1832.
Ju et al. (2006) "Four-color DNA sequencing by synthesis using cleavable fluorescent nucleotide reversible terminators" Proc. Natl. Acad. Sci., 103(52): 19635-19640.
Kahl et al. (1998) "High-Yielding Method for On-Column Derivatization of Protected Oligodeoxy-nucleotides and Its Application to the Convergent Synthesis of 5',3'-Bis-conjugates" J. Org. Chem. 63(15): 4870-4871.
Kahl et al. (1999) "Solution-Phase Bioconjugate Synthesis Using Protected Oligonucleotides Containing 3'-Alkyl Carboxylic Acids" J. Org. Chem. 64(2): 507-510.
Levine et al. (2008) "Active CMOS Sensor Array for Electrochemical Biomolecular Detection" IEEE, 43(8): 1859-1871.
Ma et al. (2013) "Isothermal amplification method for next-generation sequencing" Proc. Natl. Acad. Sci., 110(35): 14320-14323.
Mathews et al. (2016) "Photo-cleavable nucleotides for primer free enzyme mediated DNA synthesis" Organic & Biomolecular Chemistry, 14: 8278-8288.
Maurer et al. (2006) "Electrochemically Generated Acid and Its Containment to 100 Micron Reaction Areas for the Production of DNA Microarrays" PLosOne, 1: e34.
Morimoto et al. (2008) "Automatic Electrochemical Micro-pH-Stat for Biomicrosystems" Anal. Chem. 80(4): 905-914.
Organick et al. (2018) "Random access in large-scale DNA data storage" Nature Biotechnology, 36(3): 242-248.
Pon (1993) "Solid-Phase Supports for Oligonucleotide Synthesis" Methods Mol. Biol. 20: 465-496.
Ravi et al. (2018) "MiSeq: A Next Generation Sequencing Platform for Genomic Analysis" Methods Mol Biol. 1706: 223-232.
Rothberg et al. (2011) "An integrated semiconductor device enabling non-optical genome sequencing" Nature, 475: 348-352.
Schmitz et al. (1999) "Solid-Phase Enzymatic Synthesis of Oligonucleotides" Organic Lett., 1(11): 1729-1731.
Sia et al. (2003) "Microfluidic devices fabricated in poly(dimethylsiloxane) for biological studies" Electrophoresis, 24: 3563-3576.
Unger et al. (2000) "Monolithic Microfabricated Valves and Pumps by Multilayer Soft Lithography" Science, 288: 113-116.
Venkatesan et al. (1996) "Improved Utility of Photolabile Solid Phase Synthesis Supports for the Synthesis of Oligonucleotides Containing 3'-Hydroxyl Termini" J. Org. Chem. 61:525-529.
Verma et al. (1998) "Modified Oligonucleotides: Synthesis and Strategy for Users" Ann. Rev. Biochem. 67: 99-134.
Wu et al (2007) "3'-O-modified nucleotides as reversible terminators for pyrosequencing" Proc. Natl. Acad. Sci., 104 (42): 16462-16467.

\* cited by examiner

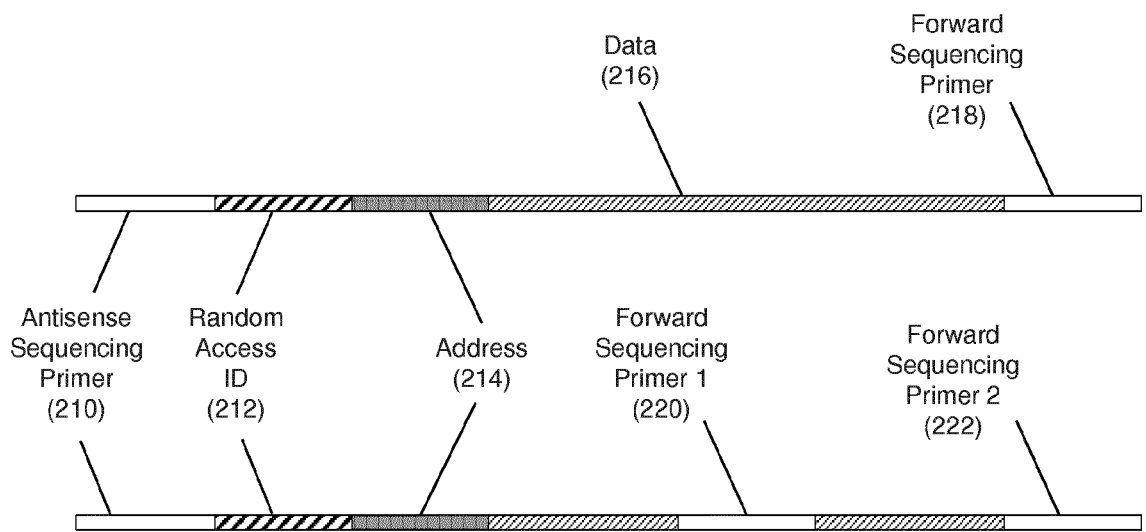

Fig. 2

| Binary: | Standard DNA: | Presence / absence | 25% combinatorial: |
| Base 2 | Base 4 | combinatorial: | Base 35 |
|  |  | Base 14 |  |

| Binary: Base 2 | Standard DNA: Base 4 | Presence/absence combinatorial: Base 14 | 25% combinatorial: Base 35 |
|---|---|---|---|
| X1 0 | X1 A | X1 A | X1 AAAA / X19 ATGG |
| X2 1 | X2 C | X2 C | X2 AAAC / X20 AGGG |
|  | X3 T | X3 T | X3 AAAT / X21 CCCC |
|  | X4 G | X4 G | X4 AAAG / X22 CCCT |
|  |  | X5 AC | X5 AACC / X23 CCCG |
|  |  | X6 AT | X6 AACT / X24 CCTT |
|  |  | X7 AG | X7 AACG / X25 CCTG |
|  |  | X8 CT | X8 AATT / X26 CCGG |
|  |  | X9 CG | X9 AATG / X27 CTTT |
|  |  | X10 TG | X10 AAGG / X28 CTTG |
|  |  | X11 ACT | X11 ACCC / X29 CTGG |
|  |  | X12 ACG | X12 ACCT / X30 CGGG |
|  |  | X13 CTG | X13 ACCG / X31 TTTT |
|  |  | X14 ACTG | X14 ACTT / X32 TTTG |
|  |  |  | X15 ACTG / X33 TTGG |
|  |  |  | X16 ACGG / X34 TGGG |
|  |  |  | X17 ATTT / X35 GGGG |
|  |  |  | X18 ATTG |

Fig. 3

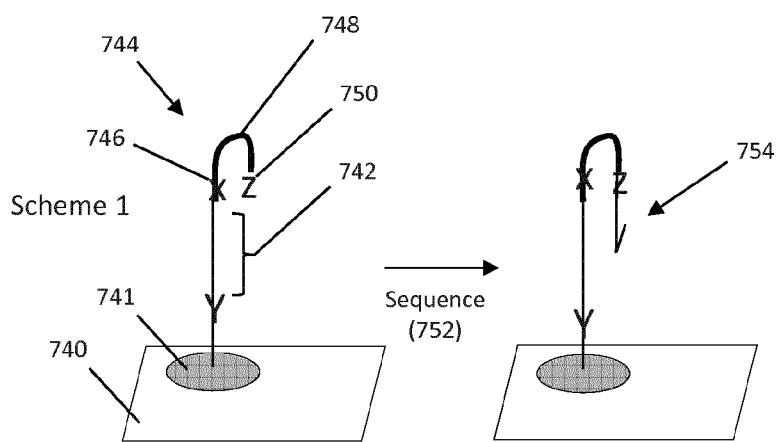
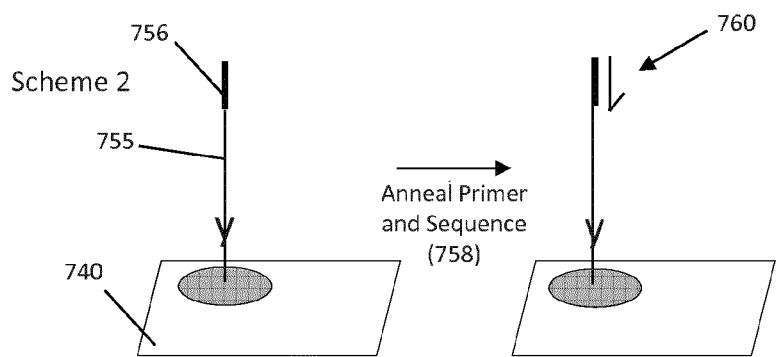
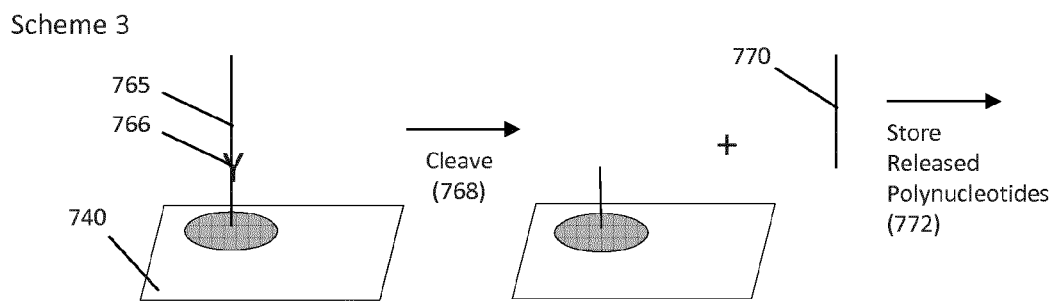
Fig. 7C

SEQUENCE LISTING

<160> NUMBER OF SEQ ID NOS: 1

<210> SEQ ID NO 1
<211> LENGTH: 381
<212> TYPE: PRT
<213> ORGANISM: artificial sequence
<220> FEATURE:
<223> OTHER INFORMATION: mutant terminal deoxynucleotidyl transferase

<400> SEQUENCE: 1

```
Asn Ser Ser Pro Ser Pro Val Pro Gly Ser Gln Asn Val Pro Ala Pro
1               5                   10                  15

Val Val Lys Lys Ile Ser Gln Tyr Ala Cys Gln Arg Arg Thr Thr Leu
            20                  25                  30

Asn Asn Tyr Asn Gln Leu Phe Thr Asp Ala Leu Asp Ile Leu Ala Glu
        35                  40                  45

Asn Asp Glu Phe Arg Glu Asn Glu Gly Ser Cys Leu Ala Phe Arg Arg
    50                  55                  60

Ala Ser Ser Val Leu Lys Ser Leu Pro Phe Pro Ile Thr Ser Met Lys
65                  70                  75                  80

Asp Thr Glu Gly Ile Pro Cys Leu Gly Asp Lys Val Lys Ser Ile Ile
                85                  90                  95

Glu Gly Ile Ile Glu Asp Gly Glu Ser Ser Glu Val Lys Ala Val Leu
            100                 105                 110

Asn Asp Glu Arg Tyr Lys Ser Phe Lys Leu Phe Thr Ser Val Phe Gly
        115                 120                 125

Val Gly Leu Lys Thr Ala Glu Lys Trp Phe Arg Met Gly Phe Arg Thr
    130                 135                 140

Leu Ser Lys Ile Gln Ser Asp Lys Ser Leu Arg Phe Thr Gln Met Gln
145                 150                 155                 160

Lys Ala Gly Phe Leu Tyr Tyr Glu Asp Leu Val Ser Gly Val Asn Arg
                165                 170                 175

Pro Glu Ala Glu Ala Val Ser Met Leu Val Lys Glu Ala Val Val Thr
            180                 185                 190

Phe Leu Pro Asp Ala Leu Val Thr Met Thr Gly Gly Phe Arg Leu Gly
        195                 200                 205

Lys Met Thr Gly His Asp Val Asp Phe Leu Ile Thr Ser Pro Glu Ala
    210                 215                 220

Thr Glu Asp Glu Glu Gln Gln Leu Leu His Lys Val Thr Asp Phe Trp
225                 230                 235                 240

Lys Gln Gln Gly Leu Leu Leu Tyr Cys Asp Ile Leu Glu Ser Thr Phe
                245                 250                 255

Glu Lys Phe Lys Gln Pro Ser Arg Thr Val Asp Ala Leu Asp His Phe
            260                 265                 270

Gln Lys Cys Phe Leu Ile Leu Lys Leu Asp His Pro Arg Val His Ser
        275                 280                 285

Val Lys Ser Gly Gln Gln Glu Gly Lys Gly Trp Lys Ala Ile Arg Val
    290                 295                 300

Asp Leu Val Met Cys Pro Tyr Asp Arg Arg Ala Phe Ala Leu Leu Gly
305                 310                 315                 320

Trp Thr Gly Ser Pro Gln Phe Asn Arg Asp Leu Arg Arg Tyr Ala Thr
                325                 330                 335

His Glu Arg Lys Met Met Leu Asp Asn His Ala Leu Tyr Asp Lys Thr
            340                 345                 350

Lys Arg Val Phe Leu Glu Ala Glu Ser Glu Glu Glu Ile Phe Ala His
        355                 360                 365

Leu Gly Leu Asp Tyr Ile Glu Pro Trp Glu Arg Asn Ala
    370                 375                 380
```

MASSIVELY PARALLEL ENZYMATIC SYNTHESIS OF NUCLEIC ACID STRANDS

CROSS REFERENCE TO RELATED APPLICATIONS

This application is a U.S. national stage application under 35 U.S.C. § 371 of International Application No. PCT/EP2019/068183, filed internationally on Jul. 5, 2019 which claims priority to EP 18306000.3, filed Jul. 23, 2018, the disclosure of each of which is hereby incorporated by reference in its entirety.

The present invention relates to new process for massively parallel synthesis of nucleic acid strands.

Biology can store information with extraordinary density, stability, and efficiency with the potential to outperform electronic based long-term data storage by orders of magnitude. Nature can routinely store and extract more than 3 gigabytes of information in a human cell and coordinate hierarchical delivery of information to differentiate tissues and regulate metabolic processes. However, storage and access of this information is tightly coupled to the biological processes encoded in the data; therefore, its adaptation to digital data storage is severely limited by our current abilities to read and write DNA at comparable semiconductor digital scales. Recent advances in DNA sequencing have greatly increased our reading capability with throughputs exceeding terabases of DNA per sequencing run opening the possibility to read at high throughput, although even this throughput is insufficient to achieve comparable throughput to digital systems. DNA synthesis capacity lags behind sequencing capacity by at least two orders of magnitude in terms of throughput and cost. Nevertheless, demonstrations using existing DNA synthesis and sequencing technologies have demonstrated the power of this approach for data storage, e.g. Church et al, Science, 337(6102): 1628 (2012); Organick et al, Nature Biotechnology, 36(3): 242-248 (2018); and the like. The challenge is that the dense hierarchical data storage in nature requires breakthroughs in encoding algorithms, DNA synthesis, and DNA sequencing together to deliver a true molecular based data storage capability.

In particular, current approaches to DNA data storage treat reading and writing as separate processes, so that information is encoded in DNA in the course of synthesis, the synthesized and encoded DNA strands are separately stored, and information is retrieved by selective amplification and sequencing, e.g. Bornholt et al, IEEE Micro, 37(3): 98-104 (2017). The high information storage capacity of DNA could be exploited more advantageously if DNA storage devices were available that supported on the same substrate both the writing, or synthesis, of DNA and the reading, or sequencing, of DNA.

SUMMARY OF THE INVENTION

The present invention is directed to methods of parallel template-free enzymatic synthesis of a plurality of nucleic acids; and more particularly, methods of parallel template-free enzymatic synthesis of nucleic acids with localized electrochemical de-protection steps. Localized electrochemical deprotection may be accomplished in a variety of ways including, for example, controlling of pH at a local reaction site to deprotect pH-sensitive bonds and/or controlling electrical potential, or voltage differences between a local reaction site and a reference electrode to deprotect by reducing or oxidizing a redox-sensitive protection group. In some embodiments, electrochemical deprotection is implemented locally using an electrode array, where control of the electrochemical properties of each reaction site is determined by one or more associated electrodes. In some embodiments, the invention is directed to parallel synthesis of polynucleotides on a substrate for storing information and to sequencing the same polynucleotides on the same substrate for retrieving information. In some embodiments, such sequencing is carried out using a sequencing-by-synthesis methodology that employs deoxynucleoside triphosphates (dNTPs) which may have a label removable by localized electrochemical changes and/or a 3'-O-blocking group removable by localized electrochemical changes.

It is a further purpose of the present invention to integrate multiple advanced technologies required to deliver a molecular data storage system that will be engineered, tested, and optimized with best industrial practices. This requires advanced new DNA synthesis technologies, new DNA sequencing methods, microscale manufacturing, microfluidics, and robust encoding. To this end, the present invention proposes to leverage the molecular precision and diversity of biological encoding systems by using enzymatic nucleic acid synthesis and associated biological machinery, to use microsystems and microfluidics to gain precise control over biological chemistry enabling highly parallelized synthesis, readout, and storage, and/or to use rapid design-build-test iteration, process control toolbox including design of experiments to deliver fully integrated systems rather than individual technologies.

The process of the present invention provides technical solution for the storage, retrieval and operating system. More particularly, the storage part is addressed by combining the potential of novel enzymatic DNA synthesis technologies and existing and proven highly parallelized automation approached. The retrieval part is addressed by leveraging existing "sequencing by synthesis" (SBS) technologies optimized to work with specific DNA structure, barcoding and density, in combination with the optimization of data structure. The operating system part presents a scheme for optimization of data density.

In some embodiments, the plurality of polynucleotides produced by the method of the invention may be combined to form larger fragments, such as genes for use in synthetic biology.

In some embodiments, template-free enzymatic synthesis methods of the invention may be used to append further information to pre-existing polynucleotides carrying encoded information. Such added information may correct pre-existing information, e.g. as in correcting or up-dating an address, or added information may simply negate or void the pre-existing information in some sense.

In one such embodiment, polynucleotides containing preexisting information may be seeded on reaction sites and amplified under kinetic exclusion conditions or by template walking, e.g. Ma et al, Proc. Natl. Acad. Sci., 110(35): 14320-14323 (2013); U.S. Pat. Nos. 9,476,080; 8,895,249; and the like. New information is added to the cloned polynucleotides by enzymatically coupling a predetermined sequence of nucleotides onto the ends of the cloned polynucleotides. The predetermined sequence of nucleotides may include the new information in a coded format. In some embodiments, prior to adding new information the cloned polynucleotides are sequenced in part or entirely, so that the new information added at a particular reaction site may depend on the information content extracted from the cloned polynucleotide at the particular site by the initial sequencing. In some embodiments, the cloned polynucleotides that have been augmented with new information may be cleaved from the reaction sites for storage or for further processing steps.

In some embodiments, polynucleotides may be synthesized using modified nucleotides that are more resistant to degradation than natural nucleotides, thereby increasing storage life and information integrity. In some embodiments, phosphorothioate, 2'-fluoro, or 2'-O-Me nucleotide monomers are substituted for natural nucleotide monomers, either entirely or as a proportion of the nucleotides in the synthesized strands, for example, to reduce enzymatic degradation. In some embodiments, completed polynucleotides are "capped" by phosphorylating their 3'-ends, for example, to reduce the likelihood of exonuclease digestion. In some embodiments, deamination may be reduced by employing 3'-O-protected dNTPs that also have base-protection groups on exocyclic amines, e.g. N-benzyl-dATP, N-benzyl-dCTP, N-isobutyl-dGTP, or the like, e.g. Beaucage and Iyer, Tetrahedron, 48(12): 2223-2311 (1992)(especially Table 3); Narang, Chapter 1, in Synthesis and Applications of DNA and RNA (Academic Press, Orlando, 1987); Srivastava et al, International patent publication WO2010/134992; and the like.

In some embodiments, polynucleotides with encoded information may be stored or maintained in double stranded form, which, for example, is more resistant to depurination. In other embodiments, coding schemes are selected that maximize the use dA's over other monomers and minimize the use of dT's in order to maximize resistance to depurination. In a particular such embodiment, information is encoded using only dAs, dCs and dGs. In some embodiments, methods of the invention comprising steps of synthesizing (writing) polynucleotides and sequencing (reading) polynucleotides include a step of proof-reading a newly synthesized polynucleotide by a sequencing-by-synthesis method that results in a double stranded product for storage. For later retrieval of information encoded in the polynucleotide, the sequencing strand may be melted off and subjected to a re-sequencing step.

In some embodiments, information-containing polynucleotides are stored in a carrier solution, such as, a readily available natural DNAs, such as salmon sperm DNA, a polycation, such as spermidine, polyvinylpyrrolidones, polymethylmethacrylates, or the like.

In some embodiments, methods of the invention for synthesizing a plurality of polynucleotides in parallel comprise the following steps: (a) providing a spatially addressable array of reaction sites, wherein each reaction site is operationally associated with at least one working electrode and has disposed thereon initiators attached by their 5'-ends and having a 3'-O-electrochemically labile protecting group; (b) performing for each kind of nucleotide a cycle of (i) deprotecting initiators or elongated fragments at electrodes at predetermined addresses by generating a voltage difference between each of the electrodes at the predetermined addresses and a reference electrode so that the electrochemically labile protecting group is cleaved, thereby generating free 3'-hydroxyls on the initiators or elongated fragments at the electrodes of the predetermined addresses, (ii) contacting under elongation conditions the electrodes at the predetermined addresses with a 3'-O-electrochemically labile-protected nucleoside triphosphate and a template-independent DNA polymerase so that the initiators or elongated fragments at the predetermined addresses are elongated by the incorporation of a 3'-electrochemically labile-protected nucleoside triphosphate to form 3'-O-electrochemically labile-protected elongated fragments; and (c) repeating step (b) until the array of polynucleotides of predetermined sequences is completed.

In some embodiments, the invention is directed to a method of template-free enzymatic synthesis of a polynucleotide with proofreading. Such method may be implemented with the following steps: a) providing an initiator at a reaction site operationally associated with at least one working electrode, wherein the initiator has a free 3-O-hydroxyl; b) repeating cycles of (i) contacting under elongation conditions the initiator or an elongated fragment thereof having free 3'-O-hydroxyls with a 3'-O-electrochemically labile-protected nucleoside triphosphate and a template-independent DNA polymerase so that the initiator or elongated fragment thereof is elongated by the incorporation of a 3'-electrochemically labile-protected nucleoside triphosphate to form 3'-O-electrochemically labile-protected elongated fragment; and (ii) deprotecting the elongated fragment of step (i) to form elongated fragment having a free 3'-hydroxyl, until the polynucleotide is complete and a sequencing primer binding site is appended to its 3' end; and c) annealing a sequencing primer to the sequencing primer binding site and sequencing the polynucleotide.

In some embodiments, the invention is directed to a method of storing and retrieving information on and from an array of polynucleotides. Such method may be implemented by the following steps: (a) providing a spatially addressable array of reaction sites, wherein each reaction site is operationally associated with at least one working electrode and has disposed thereon initiators attached by their 5'-ends and having a 3'-O-electrochemically labile protecting group; (b) performing for each kind of nucleotide a cycle of (i) deprotecting initiators or elongated fragments at electrodes at predetermined addresses by generating a predetermined voltage difference between each of the electrodes at the predetermined addresses and a reference electrode so that the electrochemically labile protecting group is cleaved, thereby generating free 3'-hydroxyls on the initiators or elongated fragments at the electrodes at the predetermined addresses, (ii) contacting under elongation conditions the electrodes at the predetermined addresses with a 3'-O-electrochemically labile-protected nucleoside triphosphate and a template-independent DNA polymerase so that the initiators or elongated fragments at the predetermined addresses are elongated by the incorporation of a 3'-electrochemically labile-protected nucleoside triphosphate to form 3'-O-electrochemically labile-protected elongated fragments; (c) repeating step (b) until the array of polynucleotides of predetermined sequences is completed, wherein each of the completed polynucleotides comprises in a 5' to 3' direction an information encoding region and a sequencing primer binding site at its 3' end; and (d) retrieving information from the information encoding region by annealing a sequencing primer to the sequencing primer binding site and sequencing by synthesis the completed polynucleotides at one or more reaction sites.

BRIEF DESCRIPTION OF THE DRAWINGS

FIG. 2 illustrates a design of an oligonucleotide for data storage (A) and a design of an oligonucleotide for data storage employing an intermediary primer (B).

FIG. 3 compares binary encoding (prior art), standard DNA quaternary encoding (prior art), presence/absence combinatorial encoding (mixes of bases where the data is encoded in the presence of absence of a nucleotide at each cycle) according to the invention, and 25% combinatorial encoding (mixes of bases where the data is encoded in the % of each base at each cycle—with 5 levels of % possible for each base: 0%, 25%, 75% and 100%) according to the invention.

FIGS. 7A-7D illustrates data storage techniques possible with template-free enzymatic synthesis.

DETAILED DESCRIPTION OF THE INVENTION

Figure 1A:
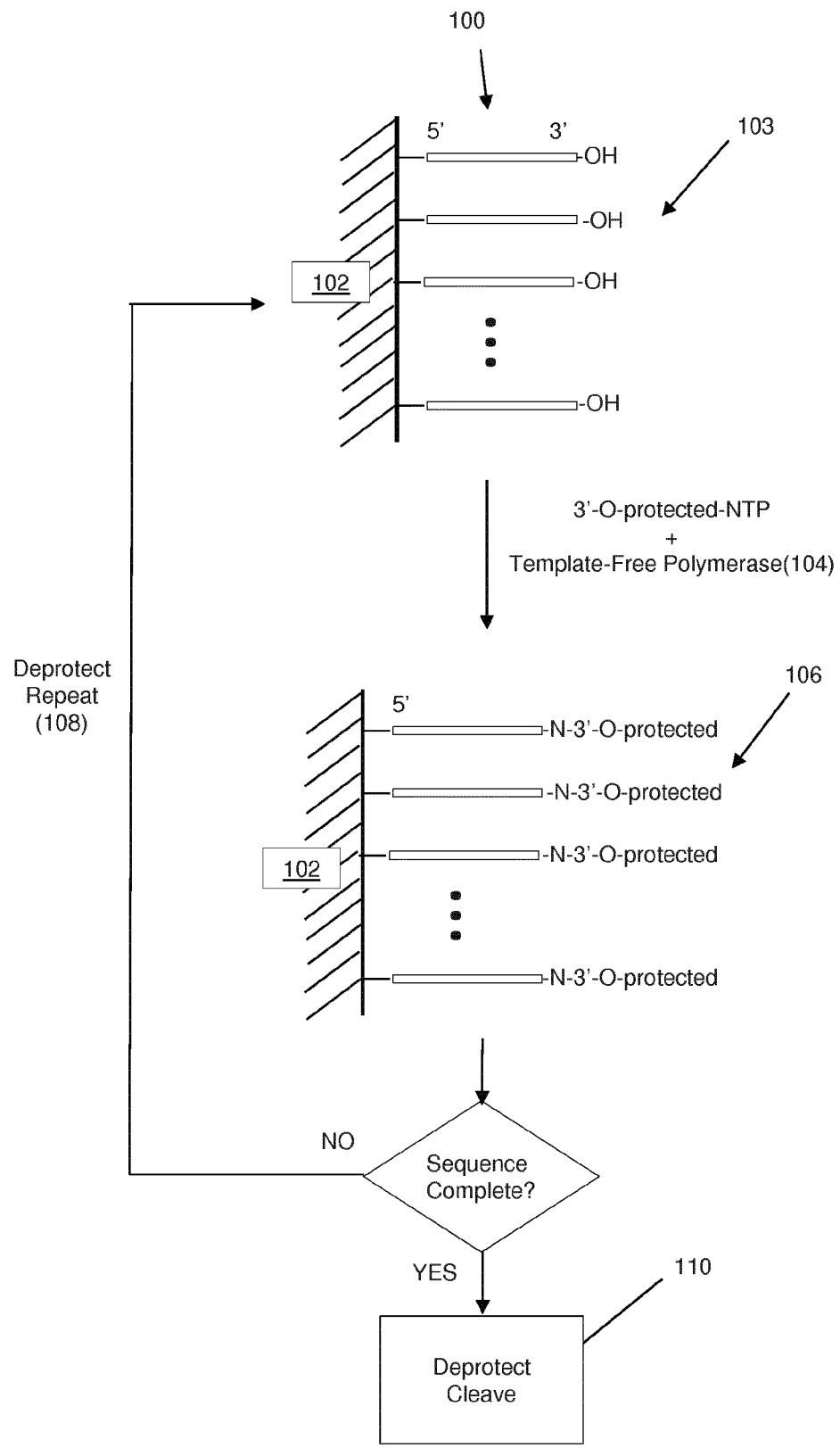
FIG. 1A contains a schematic representation of an enzymatic synthesis cycle wherein a 3'-O-protected dNTP is added to a nucleic acid strand followed by de-protection.

While the invention is amenable to various modifications and alternative forms, specifics thereof have been shown by way of example in the drawings and will be described in detail. It should be understood, however, that the intention is not to limit the invention to the particular embodiments described. The intention is to cover all modifications, equivalents, and alternatives falling within the spirit and scope of the invention. For example, the microelectronics portion of the apparatus and array is implemented in CMOS technology for purposes of illustration. It should be appreciated, however, that the disclosure is not intended to be limiting in this respect, as other semiconductor-based technologies may be utilized to implement various aspects of the microelectronics portion of the systems discussed herein. Guidance for making arrays of the invention is found in many available references and treatises on integrated circuit design and manufacturing and micromachining, including, but not limited to, Allen et al, CMOS Analog Circuit Design (Oxford University Press, 2nd Edition, 2002); Levinson, Principles of Lithography, Second Edition (SPIE Press, 2005); Doering and Nishi, Editors, Handbook of Semiconductor Manufacturing Technology, Second Edition (CRC Press, 2007); Baker, CMOS Circuit Design, Layout, and Simulation (IEEE Press, Wiley-Interscience, 2008); Veendrick, Deep-Submicron CMOS ICs (Kluwer-Deventer, 1998); Cao, Nanostructures & Nanomaterials (Imperial College Press, 2004); and the like, which relevant parts are hereby incorporated by reference. Likewise, guidance for carrying out electrochemical measurements of the invention is found in many available references and treatises on the subject, including, but not limited to, Sawyer et al, Electrochemistry for Chemists, 2nd edition (Wiley Interscience, 1995); Bard and Faulkner, Electrochemical Methods: Fundamentals and Applications, 2nd edition (Wiley, 2000); and the like, which relevant parts are hereby incorporated by reference.

In one aspect, the present invention provides a new process allowing massively parallel enzymatic synthesis of polynucleotides. As mentioned above, in one aspect, the method employs electrochemically labile protecting groups for facile parallel synthesis on large-scale electrode arrays. In one application of this process polynucleotides are used to store data which can be later retrieved from the same synthesis support by a DNA sequencing operation, for example, using a sequencing by synthesis technique, particularly one employing electrochemically labile blocking groups and/or labels.

A. Background of Enzymatic DNA Synthesis.

Recently an enzymatic synthesis process to produce very long DNA or RNA strands with the best purity has been developed (WO2015/159023). A cycle of the enzymatic synthesis process, leading to the addition of a nucleotide to a nucleic acid strand, comprises two successive steps, corresponding to an elongation step and a deprotecting step respectively (FIG. 1A). In summary, during the elongation step, the polymerase adds a nucleotide comprising a protecting group to a nucleic acid strand. Then the protection group is removed from this newly added nucleotide, to be able to perform additional cycles. This new enzymatic synthesis technology is bringing dramatic improvement to nucleic acid synthesis, as compared to chemical synthesis. The key advantages for data storage are described in the table below:

| | CHEMICAL SYNTHESIS | ENZYMATIC SYNTHESIS | ADVANTAGE FOR DATA STORAGE |
| --- | --- | --- | --- |
| CYCLE TIME | 360 s | 200 s | Throughput × 18 |
| MAX LENGTH | 200 nt | 150 nt | Data density |
| PURITY PER CYCLE | 99.5% | 99.3% | Less redundancy |
| ENVIRONMENT | Controlled | Open | Simpler device |
| HAZARDOUS CHEMICALS | Yes | No | Greener & no waste management needed |
| POST PROCESSING | Yes (multiple hours) | No | Simpler process, less Infrastructure |
| AQUEOUS MEDIA | No | Yes | Compatible with SBS |

Generally, methods of template-free enzymatic DNA synthesis comprises repeated cycles of steps, such as are illustrated in FIG. 1A, in which a predetermined nucleotide is coupled to an initiator or growing chain in each cycle. The general elements of template-free enzymatic synthesis is described in the following references: Ybert et al, International patent publication WO/2015/159023; Ybert et al, International patent publication WO/2017/216472; Hyman, U.S. Pat. No. 5,436,143; Hiatt et al, U.S. Pat. No. 5,763,594; Jensen et al, Biochemistry, 57: 1821-1832 (2018); Mathews et al, Organic & Biomolecular Chemistry, DOI: 0.1039/c6ob01371f (2016); Schmitz et al, Organic Lett., 1(11): 1729-1731 (1999).

Initiator polynucleotides (100) are provided, for example, attached to solid support (102), which have free 3'-hydroxyl groups (103). To the initiator polynucleotides (100) (or elongated initiator polynucleotides in subsequent cycles) are added a 3'-O-protected-dNTP and a template-free polymerase, such as a TdT or variant thereof (e.g. Ybert et al, WO/2017/216472) under conditions (104) effective for the enzymatic incorporation of the 3'-O-protected-dNTP onto the 3' end of the initiator polynucleotides (100) (or elongated initiator polynucleotides). This reaction produces elongated initiator polynucleotides whose 3'-hydroxyls are protected (106). If the elongated initiator polynucleotide contains a competed sequence, then the 3'-O-protection group may be removed, or deprotected, and the desired sequence may be cleaved from the original initiator polynucleotide. Such cleavage may be carried out using any of a variety of single strand cleavage techniques, for example, by inserting a cleavable nucleotide at a predetermined location within the original initiator polynucleotide. An exemplary cleavable nucleotide may be a uracil nucleotide which is cleaved by uracil DNA glycosylase. If the elongated initiator polynucleotide does not contain a completed sequence, then the 3'-O-protection groups are removed to expose free 3'-hydroxyls (103) and the elongated initiator polynucleotides are subjected to another cycle of nucleotide addition and deprotection. In accordance with on aspect of the invention, 3'-O-protection groups are electrochemically labile groups. That is, deprotection or cleavage of the protection group is accomplished by changing the electrochemical conditions in the vicinity of the protection group which result in cleavage. Such changes in electrochemical conditions may be brought about by changing or applying a physical quantity, such as a voltage difference or light to activate auxiliary species which, in turn, cause changes in the electrochemical conditions at the site of the protection group, such as an increase or decrease in pH. In some embodiments, electrochemically labile groups include, for example, pH-sensitive protection groups that are cleaved whenever the pH is changed to a predetermined value. In other embodiments, electrochemically labile groups include protecting groups which are cleaved directly whenever reducing or oxidizing conditions are changed, for example, by increasing or decreasing a voltage difference at the site of the protection group.

As used herein, an "initiator" (or equivalent terms, such as, "initiating fragment", "initiator nucleic acid", "initiator oligonucleotide", or the like) usually refers to a short oligonucleotide sequence with a free 3'-end, which can be further elongated by a template-free polymerase, such as TdT. In one embodiment, the initiating fragment is a DNA initiating fragment. In an alternative embodiment, the initiating fragment is an RNA initiating fragment. In some embodiments, an initiating fragment possesses between 3 and 100 nucleotides, in particular between 3 and 20 nucleotides. In some embodiments, the initiating fragment is single-stranded. In alternative embodiments, the initiating fragment is double-stranded. In some embodiments, an initiator may comprise a non-nucleic acid compound having a free hydroxyl to which a TdT may couple a 3'-O-protected dNTP, e.g. Baiga, U.S. patent publications US2019/0078065 and US2019/0078126.

Returning to FIG. 1A, in some embodiments, an ordered sequence of nucleotides are coupled to an initiator nucleic acid using a template-free polymerase, such as TdT, in the presence of 3'-O-protected dNTPs in each synthesis step. In some embodiments, the method of synthesizing an oligonucleotide comprises the steps of (a) providing an initiator having a free 3'-hydroxyl; (b) reacting under extension conditions the initiator or an extension intermediate having a free 3'-hydroxyl with a template-free polymerase in the presence of a 3'-O-protected nucleoside triphosphate to produce a 3'-O-protected extension intermediate; (c) deprotecting the extension intermediate to produce an extension intermediate with a free 3'-hydroxyl; and (d) repeating steps (b) and (c) until the polynucleotide is synthesized. (The terms "extension intermediate," "extension product" and "elongation fragment" are used interchangeably). In some embodiments, an initiator is provided as an oligonucleotide attached to a solid support, e.g. by its 5' end. The above method may also include washing steps after the reaction, or extension, step, as well as after the de-protecting step. For example, the step of reacting may include a sub-step of removing unincorporated nucleoside triphosphates, e.g. by washing, after a predetermined incubation period, or reaction time. Such predetermined incubation periods or reaction times may be a few seconds, e.g. 30 sec, to several minutes, e.g. 30 min.

The 3'-O-blocked dNTPs employed in the invention may be purchased from commercial vendors or synthesized using published techniques, e.g. U.S. Pat. No. 7,057,026; Guo et al, Proc. Natl. Acad. Sci., 105(27): 9145-9150 (2008); Benner, U.S. Pat. No. 7,544,794.

The above method may also include capping step(s) as well as washing steps after the reacting, or extending, step, as well as after the deprotecting step. As mentioned above, in some embodiments, capping steps may be included in which non-extended free 3'-hydroxyls are reacted with compounds that prevents any further extensions of the capped strand. In some embodiments, such compound may be a dideoxynucleoside triphosphate. In other embodiments, non-extended strands with free 3'-hydroxyls may be degraded by treating them with a 3'-exonuclease activity, e.g. Exo I. For example, see Hyman, U.S. Pat. No. 5,436,143. Likewise, in some embodiments, strands that fail to be deblocked may be treated to either remove the strand or render it inert to further extensions.

In some embodiments, reaction conditions for an extension or elongation step may comprising the following: 2.0 µM purified TdT; 125-600 µM 3'-O-protected dNTP (e.g. 3'-O—$NH_2$-protected dNTP); about 10 to about 500 mM potassium cacodylate buffer (pH between 6.5 and 7.5) and from about 0.01 to about 10 mM of a divalent cation (e.g. $CoCl_2$ or $MnCl_2$), where the elongation reaction may be carried out in a 50 µL reaction volume, at a temperature within the range RT to 45° C., for 3 minutes.

Enzymatic nucleic acid synthesis enables to synthesize longer and purer DNA fragments, faster than chemistry. The cycle time factor is particularly interesting for data storage as it enables to increase the throughput 15 to 20-fold. Performing the synthesis in aqueous media also makes it greener (no organic solvents used during synthesis), simplifies instrumentation (no need to control the environment) and eliminates the need for chemical waste management facilities.

The present invention now proposes to improve this enzymatic synthesis process to allow massively parallel synthesis. In a first aspect, the present invention provides a process compatible with pH controlled deprotection.

B. Approaches to Parallel Enzymatic Polynucleotide Synthesis.

In one aspect, the invention provides methods and apparatus for highly parallel template-free enzymatic synthesis of a plurality of different polynucleotides each having a predetermined sequence of nucleotides. In some embodiments, parallel synthesis is implemented by providing a support having discrete, non-overlapping, addressable sites where separate polynucleotides are synthesized and a means for controlling electrochemical conditions at each site independently of the other sites is provided. In some embodiments, such parallel synthesis support is a planar support having a regular pattern of addressable sites, such as, a rectilinear pattern of sites, or a hexagonal pattern of sites. In some embodiments, each site of a planar support is associated with one or more electrodes whose electrical characteristics may be controlled in an addressable manor independent of other electrodes of the planar support. In some embodiments, such planar supports have a plurality of sites comprising at least 256 sites, at least 512 sites, at least 1024 sites, at least 5000 sites, at least 10,000 sites, at least 25,000 sites, or at least 100,000 sites and as many as 10,000,000 sites. In some embodiments, such planar supports have a plurality of sites greater than 1000, or 10,000, or 25,000, or 50,000, or 100,000, or 500,000, and up to 1,000,000 sites or up to 10,000,000 sites. In some embodiments, the sites of such planar supports are disposed in a regular array and each site is associated with at least one electrode integrated with the planar support. In some embodiments, the discrete site at which synthesis and/or sequencing take place each has an area in the range of from 0.25 $\mu m^2$ to 1000 $\mu m^2$, or from 1 $\mu m^2$ to 1000 $\mu m^2$, or from 10 $\mu m^2$ to 1000 $\mu m^2$, or from 100 $\mu m^2$ to 1000 $\mu m^2$. In some embodiments, the amount of polynucleotides synthesized at each site is at least $10^{-6}$ fmol, or at least $10^{-3}$ fmol, or at least 1 fmol, or at least 1 pmol, or the amount of polynucleotide synthesized at each site is in the range of from $10^{-6}$ fmol to 1 fmol, or from $10^{-3}$ fmol to 1 fmol, or from 1 fmol to 1 pmol, or from $10^{-6}$ pmol to 10 pmol, or from $10^{-6}$ pmol to 1 pmol. In some embodiments, the number of polynucleotides synthesized at each site is in the range of from 1000 molecules to $10^6$ molecules, or from 1000 molecules to $10^9$ molecules, or from 1000 molecules to $10^{12}$ molecules.

In some embodiments, enzymatically synthesized polynucleotides at each reaction site have lengths in the range of from 50 to 500 nucleotides; in other embodiments, such polynucleotides have lengths in the range of from 50 to 1000 nucleotides.

Figure 1B:
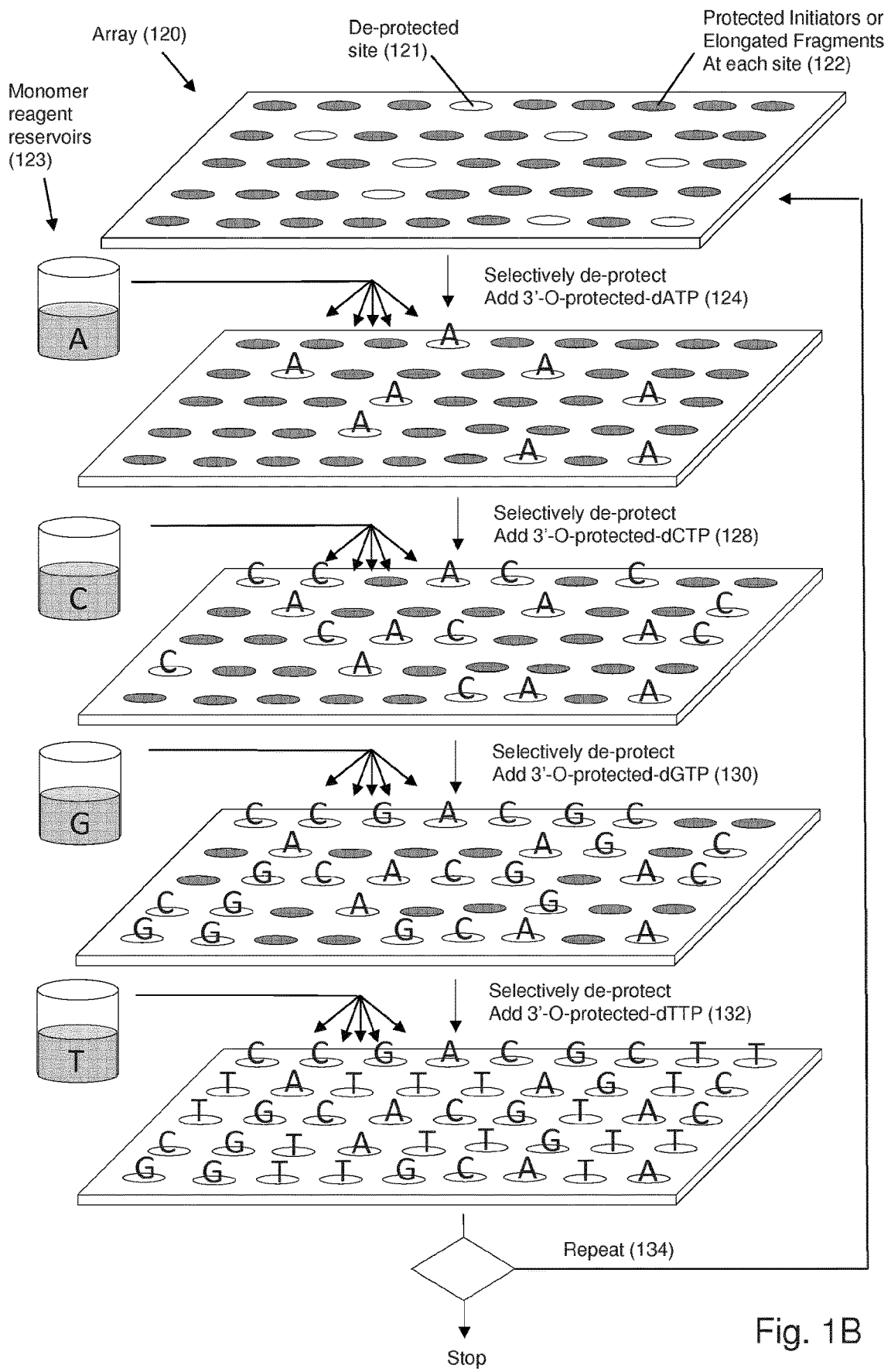
FIG. 1B illustrates the steps of one embodiment of the invention for parallel template-free enzymatic synthesis of a plurality of polynucleotides on an addressable electrode array.

FIG. 1B illustrates the steps for one embodiment of parallel synthesis of a plurality of polynucleotides on discrete sites addressable either for specific photo-illumination or for electrode activation. In some embodiments, the array is an addressable electrode array in which individual electrodes may be controlled to generate a predetermined voltage difference between any given working electrode of the array and a counter electrode. Array (120) is provided such that each site (122) has an initiator or an elongated fragment with a protected 3'-hydroxyl (represented as the dark disks). To initiate a synthesis cycle, the 3'-hydroxyls of initiators or elongated fragments of selected sites (the ones corresponding to polynucleotides for which the next monomer is A) are deprotected (121) (represented as open disks) using a deprotection method that can be restricted to the location of the selected sites. As described more fully below, in some embodiments, such localized deprotection may be effected by localized photoreactions or by localized changes in voltage differences using site-specific electrodes. To the selectively deprotected sites is added a reagent comprising 3'-O-protected-dATPs (124) and a template-free polymerase, such as a TdT, is delivered to the deprotected sites. As described briefly below, the synthesis reagents may be delivered in a variety of ways, such as, by simple bulk flow over the entire array, droplets delivered by an inkjet device to individual sites, or the like. After a predetermined time for the coupling reaction to advance to completion or to a suitable extent, the array is washed and the next group of polynucleotides (those for which C is the next monomer) at selected sites have their 3'-hydroxyls deprotected. To the selectively deprotected sites is added a reagent comprising 3'-O-protected-dCTPs (128) and a template-free polymerase, such as a TdT, is delivered to the deprotected sites. Similar steps are performed for dGTPs (130) and dTTPs (132), until the cycle is completed. The cycles are repeated (134) until the polynucleotides are completed.

Photo-Induced Deprotection.

In some embodiments, the process of the invention uses photo induced deprotection with a photogenerated acid to locally deprotect, e.g. Gao et al, U.S. Pat. Nos. 6,426,184, 7,491,680 and 7,838,466. Advantageously, the oligonucleotides are synthesized in a flow cell, very similar to those used for Sequencing by Synthesis (SBS) today. SBS uses modified dNTPs containing a terminator which blocks further polymerization. So only a single base can be added by a polymerase enzyme to each growing DNA or RNA copy strand. The sequencing reaction is conducted simultaneously on a very large number of different template molecules spread out on a solid surface. Following the addition of the four dNTPs to the templates, the terminators are removed. This chemistry is called "reversible terminators". Finally, another four cycles of dNTP additions are initiated. Since single bases are added to all templates in a uniform fashion, the sequencing process produces a set of DNA/RNA sequence reads of uniform length. Advantageously, the DNA/RNA sample is prepared into a "sequencing library" by the fragmentation into pieces each around 200 bases long. Custom adapters are added to each end and the library is flowed across a solid surface (the "flow cell") and the template fragments bind to this surface. Following this, a solid phase "bridge amplification" PCR process (cluster generation) creates approximately one million copies of each template in tight physical clusters on the flowcell surface.

In some embodiments of the present invention, the chip can be directly read after synthesis by SBS to ensure successful encoding. In some embodiments, the chips can be approximately 50 $cm^2$. The chip has a grid of microwells at a 30 $\mu m$, 5 $\mu m$, or even 1 $\mu m$. With a 5 $\mu m$ pitch, the total number of wells is then 200 million, with 1 $\mu m$ pitch, the chip has 5 billion microwells. The oligonucleotides can be grafted directly on the bottom of the wells or on beads which would be filled in the chip in such a way that there is one and only one bead per chip. Deprotection may be effected by controlled by photo-generated acid in selected wells by using a Digital Micromirror Device (DMD).

In some embodiments, the oligonucleotides synthesized will be up to 400 nucleotides in length, as this is the maximum length easily readable by Sequencing By Synthesis using dual paired ends reads. Increasing the length of oligos above chemistry 200 nt enables higher data density on the chip as data density as indexing will take a lower percentage of the oligonucleotide. Alternatively, and if synthesis purity enables it, it could be possible to increase the length synthesized and add intermediate primers every 200 nucleotides to ease sequencing to sequence sequentially the oligonucleotides.

One Flow cell with 5 μm distance between wells enables the following:
  200 million oligonucleotides of 400 nt in parallel
  7 h to print the whole chip (80 000 000 000 nt)
  1.5 bit per cycle in encoding system (see below)
  15 GB per flow cell With a 1 μm pitch between wells (5 billion oligonucleotides in parallel), the amount of data stored is 375 GB, performing this run 3 times enables to synthesize more than 1 TB in one instrument.

The flow cell is preferably transparent for allowing UV deprotection and sequencing. The number of DMDs needed can be advantageously of at least 50. Preferably, the number of DMDs is more than 50, to increase number of wells and use confocal lenses in order to reduce pitch to 1 μm and increase density.

One challenge in the generation of local pH changes is the diffusion of H3O+ ions. To prevent contamination, pH should be as stable as possible in the wells that are not illuminated and in the illuminated well during deprotection. Advantageously, during deprotection, the pH in the illuminated well is between 4.5 and 5.8, while the pH is maintained around 6 in non-illuminated wells.

To further increase the quantity of data stored, it is possible to develop photolabile nucleotides that are deprotected very quickly (up to about 1 sec deprotection). Since the enzymatic technology is very robust and can be used in open environment, it is also possible to synthesis DNA/RNA on tapes instead of flow cells.

Electrochemical Deprotection.

Alternatively or in addition to local photochemical generation of pH changes, controlled changes in electrical potential at an electrode can be used to directly or indirectly cleave electrochemically labile groups. For example, pH-sensitive protection groups may be indirectly cleaved using voltage changes by employing an electroactive compound whose redox state may be changed by controlling local voltage differences, thereby liberating electrons which affect local pH, e.g. Southern, U.S. Pat. No. 5,667,667; Egeland and Southern, U.S. patent publication US2004/0238369; Egeland et al, Nucleic Acids Research, 33(14): e125 (2005); Maurer et al, U.S. Pat. No. 9,267,213; Fomina et al, LabChip, 16: 2236-2244 (2016), Moreover, chips enabling electrochemical deprotection on a large scale can be used, for example, by employing electrode arrays fabricated using CMOS chip technology or other semiconductor technology. Advantages of this technology include:
  Pitch reduction to permit massively large-scale synthesis
  Stackability of chips
  Synthesis and storage on 1 μm beads
  Sequencing using semiconductor sequencing platforms, such as Ion Torrent CMOS chips provide control to every synthesis sites by generating current or light to individually accessible sites. The current or light induced can be couple with respectively electrochemistry or photochemistry to generate locally protons in order to decrease the pH. In some embodiments, both photochemically generated acid and electrochemically generated acids is used to deprotect 3'-hydroxyls in the synthesis and/or sequencing process.

Figure 6A:
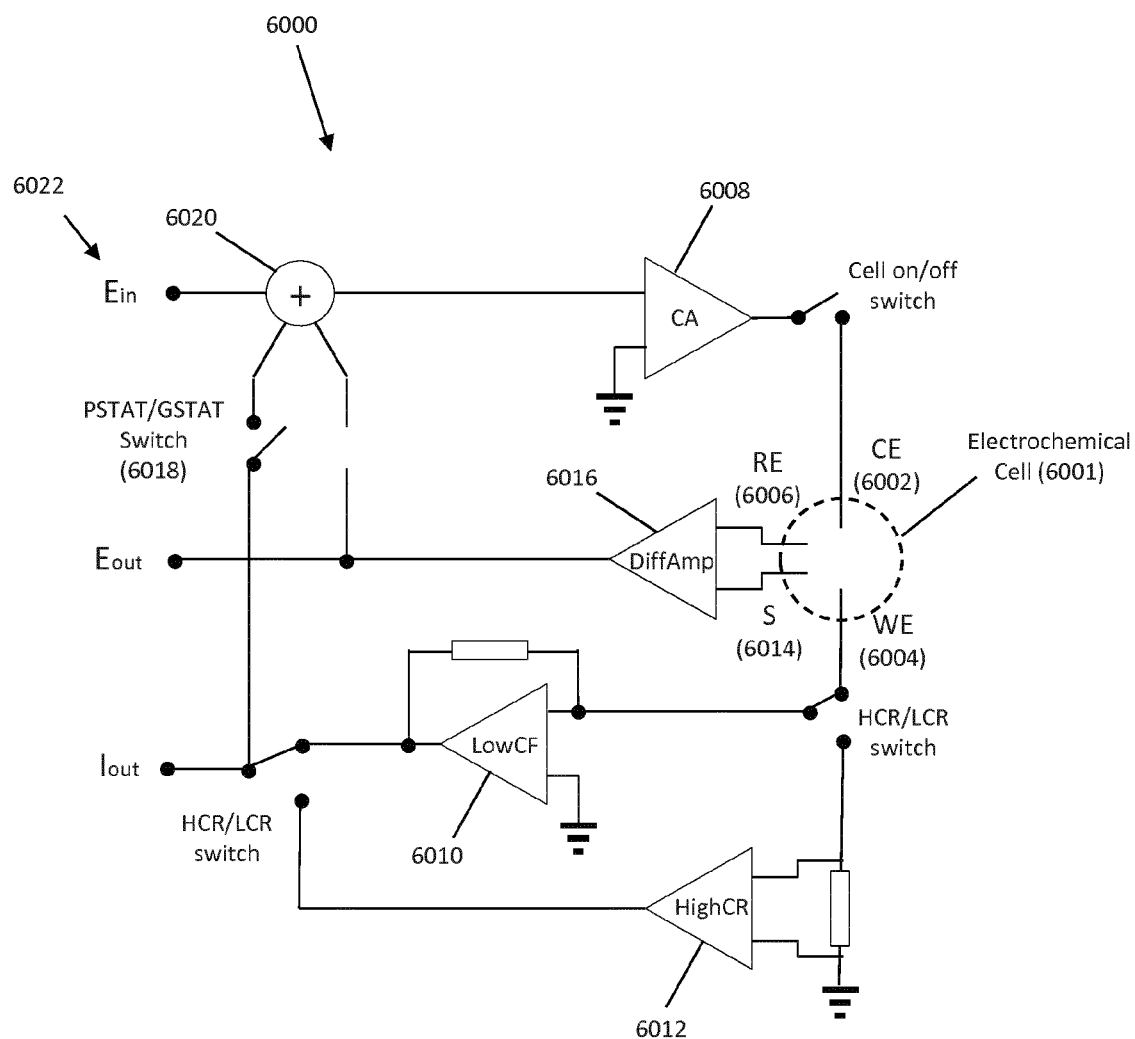
FIG. 6A is an embodiment of a potentiostat electronic circuit for controlling electrochemical conditions at an electrode.

In some embodiments, each site on an electrode array may be configured as a potentiostat and/or galvanostat electrochemical cell (6001) as described by Levine et al (cited above) or Metrohm application note EC08. In potentiostatic mode, a potentiostat/galvanostat (PGSTAT) circuit (6000) as illustrated in FIG. 6A will accurately control the potential of Counter Electrode (CE) (6002) against the Working Electrode (WE) (6004) so that the potential difference between the working electrode (WE) (6004) and the Reference Electrode (RE) (6006) is well defined, and correspond to the value specified by the user. In galvanostatic mode, the current flow between the WE (6004) and the CE (6002) is controlled. The potential difference between the RE (6006) and WE (6004) and the current flowing between the CE (6002) and WE (6004) are continuously monitored. By using a PGSTAT, the value specified by the user (i.e. applied potential or current) is accurately controlled, anytime during the measurement by using a negative feedback mechanism.

As can be seen from the diagram, the CE (6002) is connected to the output of an electronic block referred to as a Control Amplifier (CA)(6008). The control amplifier forces current to flow through the cell. The value of the current is measured using a Current Follower (LowCF) (6010) or a Shunt (HighCR) (6012), for low and high currents, respectively. The potential difference is measured always between the RE (6006) and S (6014) with a Differential Amplifier (Diffamp)(6016). Depending on the mode the instrument is used (potentiostatic or galvanostatic) the PSTAT/GSTAT switch (6018) is set accordingly. The signal is then fed into the Summation Point (+) (6020) which, together with the waveform set by a digital-to-analog converter (Ein) (6022) will be used as an input for the control amplifier.

A counter electrode (also known as auxiliary electrode), is an electrode which is used to close the current circuit in the electrochemical cell. It is usually made of an inert material (e.g. Pt, Au, graphite, glassy carbon) and usually it does not participate in the electrochemical reaction. Because the current is flowing between the WE (6004) and the CE (6002), the total surface area of the CE (source/sink of electrons) is typically larger than the area of the WE so that it will not be a limiting factor in the kinetics of the electrochemical process.

A reference electrode is an electrode which has a stable and well-known electrode potential and it is used as a point of reference in the electrochemical cell for the potential control and measurement. The high stability of the reference electrode potential is usually reached by employing a redox system with constant (buffered or saturated) concentrations of each participants of the redox reaction. Moreover, the current flow through the reference electrode is kept close to zero (ideally, zero) which is achieved by using the CE to close the current circuit in the cell together with a very high input impedance on the electrometer (>100 GOhm).

The working electrode is the electrode in an electrochemical system on which the reaction of interest is occurring. Common working electrodes can be made of inert materials such as Au, Ag, Pt, glassy carbon (GC) and Hg drop and film electrodes etc. Working electrode (6004) may comprise a coating for attaching molecules, such as initiators for template-free enzymatic polynucleotide synthesis.

Two electrode setup. In a two-electrode cell setup, CE (6002) and RE (6006) are shorted on one of the electrodes while the WE (6004) and S (6014) are shorted on the opposite electrode. The potential across the complete cell is measured. This includes contributions from the CE/electrolyte interface and the electrolyte itself. The two-electrode configuration can therefore be used whenever precise control of the interfacial potential across the WE (6004) electrochemical interface is not critical and the behavior of the whole cell is under investigation.

Three electrode setup. The three-electrode cell setup is the most common electrochemical cell setup used in electrochemistry. In this case, the current flows between the CE (6002) and the WE (6004). The potential difference is controlled between the WE (6004) and the CE (6002) and measured between the RE (6006) (preferably kept at close proximity of the WE (6004)) and S (6014). Because the WE (6004) is connected with S (6014) and WE (6004) is kept at pseudo-ground (fixed, stable potential), by controlling the polarization of the CE (6002), the potential difference between RE (6006) and WE (6004) is controlled all the time. The potential between the WE (6004) and CE (6002) usually is not measured. This is the voltage applied by the control amplifier (6008) and it is limited by the compliance voltage of the instrument. It is adjusted so that the potential difference between the WE (6004) and RE (6006) will be equal to the potential difference specified by the user. This configuration allows the potential across the electrochemical interface at the WE (6004) to be controlled with respect to the RE (6006).

Large-scale electrode arrays comprising a plurality of individually addressable electrodes formed in a circuit-supporting substrate, especially CMOS, have been constructed for phosphoramidite-based synthesis and for sensor applications, e.g. Montgomery, U.S. Pat. Nos. 6,093,302, 6,444,111 and 6,280,595; Gindilis, U.S. Pat. No. 9,339,782; Maurer et al, U.S. Pat. No. 9,267,213; Maurer et al, PLosOne, December 2006, issue 1, e34; Fomina et al, LabChip, 16: 2236-2244 (2016); Kavusi et al, U.S. Pat. No. 9,075,041; Johnson et al, U.S. Pat. Nos. 9,874,538 and 9,910,008; Gordon et al, U.S. Pat. No. 6,251,595; Levine et al, and the like. IEEE J. Solid State Circuits, 43: 1859-1871 (2008); and the like. These references provide guidance for the design of particular embodiments of the present invention with respect to such features as electrode numbers, size, composition and configurations at array sites; CMOS circuitry for voltage and current control and measurement; array fabrication and operation; methodologies for attaching or immobilizing chemical components (such as, for example, initiators) at array sites; and the like.

Of particular interest are the electrode configurations described in Morimoto et al, Anal. Chem. 80: 905-914 (2008); Levine et al (cited above); and Fomina et al (cited above) and their implementation with CMOS technology, particularly as described by Levine et al and Fomina et al. In some embodiments of the invention, an electrode array is provided comprising a plurality of individually addressable working electrodes in a CMOS substrate, which is operationally associated with a reference electrode and a counter electrode, the latter of which may be onboard or separate from the CMOS electrode array. CMOS circuitry is configured so that the voltage between the working electrodes and the counter electrode (s) may be adjusted to establish and maintain a desired voltage difference between selected working electrodes and the reference electrode. The desired voltage differences may be changed at selected working electrodes to cleave electrochemically labile protecting groups.

Combination of Enzymatic Synthesis and Electrochemical Deprotection.

In one aspect, the present invention also provides a solution for combining the different ways to induced specially controlled deprotection, through pH decrease, with enzymatic DNA synthesis technology. Enzymatic synthesis is fully compatible with aqueous media. Most of the chemistry, electrochemistry or photochemistry, enabling a pH change though physical actuation are working only in aqueous media. The invention is providing technical solution to make these two aspects compatible by developing the appropriate chemistry for pH change and the appropriate buffers, reagents and protection groups for the enzymatic synthesis. So, in one of the embodiment the controllable chemistry is compatible with DNA synthesis and with the flow-cell chip surface chemistry.

Electrochemical, or Induced, deprotection, that is, the use of voltage changes at an electrode adjacent to a reaction site, has been employed to remove DMT protection groups in phosphoramidite-based synthesis, e.g. Egeland et al, Nucleic Acids Research, 33(14): e125 (2005); Montgomery (cited above). The invention in part is a discovery and recognition that parallel template-free enzymatic polynucleotide synthesis could be accomplished using electrochemical deprotection of protecting groups specific for enzymatic synthesis. In particular, 3'-O-azidomethyl protecting groups may be cleaved by direct reduction and 3'-O-amino protecting groups may be cleaved indirectly by adjusting local pH by way of an electroacive intermediary compound. For example, in the case of the latter, in some embodiments, a typical deprotection solution is 700 mM sodium nitrite (NaNO2) and 1 M sodium acetate titrated to pH 5.0-5.5 with HCl. Local deprotection of 3'-O—NH2 groups at a reaction site of an array may be effected by lowering the local pH from pH 7 to pH 5.

Apparatus for implementing methods of the invention. Components of an apparatus for implementing a method of the invention are illustrated diagrammatically in FIG. 6B. Flow cell and electrode array (600) comprise an array of reaction sites each of which may include a microwell, coatings to enhance attachment of initiators or other components and each of which is operationally associated with one or more electrodes. In some embodiments, the electrode array is integrated with CMOS control and measurement circuitry as a single chip. A flow cell can have a variety of designs for controlling the path and flow rate of reagents over the electrode array. In some embodiments, a flow cell is a microfluidics device. That is, it may be fabricated with micromachining techniques or precision molding to include additional fluidic passages, chambers, and so on. In one aspect, a flow cell comprises an inlet (602), an outlet (603), and a flow chamber (605) for defining the flow path of reagents over electrode array (607). Reagents are discarded into a waste container (606) after exiting flow cell and sensor array (600). In accordance with this embodiment, a function of the apparatus is to deliver different reagents to flow cell and electrode array (600) in a predetermined sequence, for predetermined durations, at predetermined flow rates, and optionally to measure physical and/or chemical parameters at the electrode sites that provide information about the status of a reaction taking place therein. To this end, fluidics controller (618) controls by lines (620 and 622) the driving forces for a plurality of reagents (614) (for example, 3'-O-protected dNTPs and/or template-free polymerase in appropriate buffers and deprotection solution(s)) and the operation of valves (for example, 612 and 616) by conventional instrument control software, e.g. Lab View (National Instruments, Austin, Tex.).

The reagents may be driven through the fluid pathways, valves and flow cell by pumps, by gas pressure, or other conventional methods. In some embodiments, a single reference electrode (608) may be positioned upstream of flow cell and sensor array (600). In other embodiments, a reference electrode may be positioned within the flow chamber.

In some embodiments, a single fluid or reagent is in contact with reference electrode (608) throughout an entire multi-step reaction. This may be achieved with the configuration illustrated in FIG. 6B where reagents (614) are directed through passage (609) to flow cell (605). When those reagents are flowing, valve (612) is shut, thereby preventing any wash solution from flowing into passage (609). Although the flow of wash solution is stopped, there is still uninterrupted fluid and electrical communication between reference electrode, passage (609), and electrode array (607). At most reagents (614) when flowing through passage (609) diffuse into passage (611), but the distance between reference electrode (608) and the junction between passages (609) and (611) is selected so that little or no amount of the reagents flowing in common passage (609) reach reference electrode (608). Although FIG. 6B and other figures illustrate an electrode (for example, reference electrode, 608) as a cylinder concentric with a fluid passage (for example, 611), reference electrodes, such as (608), may have a variety of different shapes. For example, it could be a wire inserted into the lumen of (611). In one aspect, reference electrode (608) constitutes a section of passage (612) that is made of a conductive material, such as stainless steel, gold, or the like. In some embodiments, the material is inert with respect to reagents in contact with it. Reference electrode (608) in one embodiment is a tube made of a conductive material which forms part of passage (612).

Figure 6B:
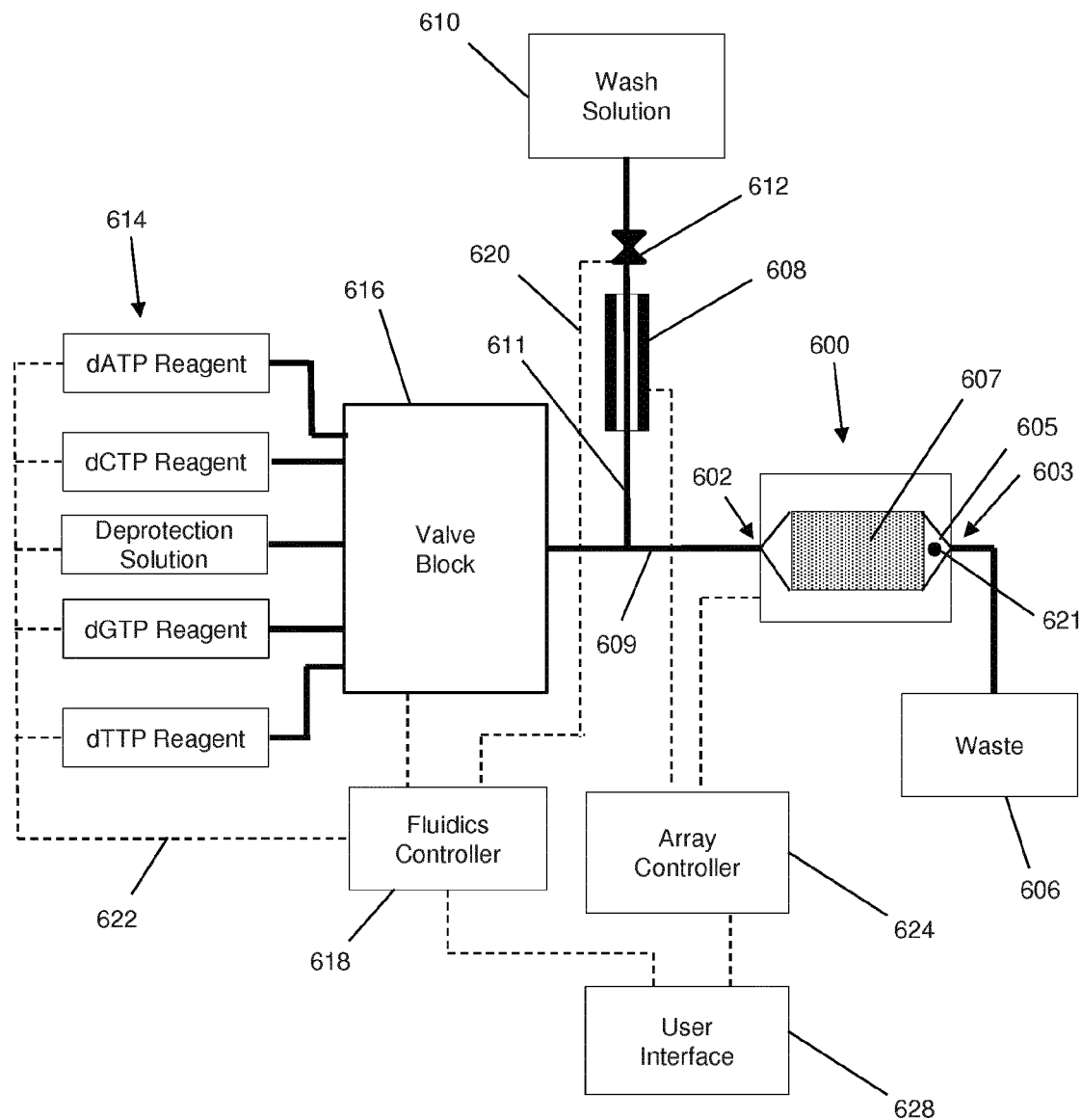
FIG. 6B illustrates diagrammatically an embodiment of an apparatus for synthesizing polynucleotides on an electrode array in which reagents are flowed across the array in sequence.

The potential of the reference voltage depends on the interface between the electrode and the solution in which the electrode is in contact. For example, solutions of different nucleoside triphosphates may cause the reference voltage to change, thereby causing undesirable changes at the working electrodes. For multi-step reactions using frequent wash steps, wash solution (610) may be selected as the reagent in continuous contact with reference electrode (608) as illustrated in FIG. 6B.

Further components of this embodiment include array controller (624) for providing bias voltages (such as to control the potential between working electrodes and counter electrodes (621), which may or may not be integral with array (607)) and timing and control signals to the electrode array (if such components are not integrated into the electrode array), and for collecting and/or processing output signals. Information from flow cell and electrode array (600), as well as instrument settings and controls may be displayed and entered through user interface (628). For some embodiments, for example, nucleic acid synthesis and/or sequencing, the temperature of flow cell and sensor array (600) is controlled so that reactions take place and measurements are made at a known, and preferably, predetermined temperatures. Such temperature may be controlled by conventional temperature control devices, such as, a Peltier device, or the like. In one aspect, temperature is conveniently controlled by controlling the temperatures of the reagents flowing through the flow cell. Flow cells and fluidic circuits of the apparatus may be fabricated by a variety of methods and materials. Factors to be considered in selecting materials include degree of chemical inertness required, operating conditions, e.g. temperature, and the like, volume of reagents to be delivered, whether or not a reference voltage is required, manufacturability, and the like. For small scale fluid deliveries, microfluidic fabrication techniques are well-suited for making fluidics circuits of the invention, and guidance for such techniques is readily available to one of ordinary skill in the art, e.g. Malloy, Plastic Part Design for Injection Molding: An Introduction (Hanser Gardner Publications, 1994); Herold et al, Editors, Lab-on-a-Chip Technology (Vol. 1): Fabrication and Microfluidics (Caister Academic Press, 2009); and the like. For meso-scale and larger scale fluid deliveries, conventional machining techniques may be used to fabricate parts that may be assembled into flow cells or fluidic circuits of the invention. In one aspect, plastics such as polycarbonate, polymethyl methacrylate, and the like, may be used to fabricate flow cells and fluidics circuits of the invention.

Figure 6C:
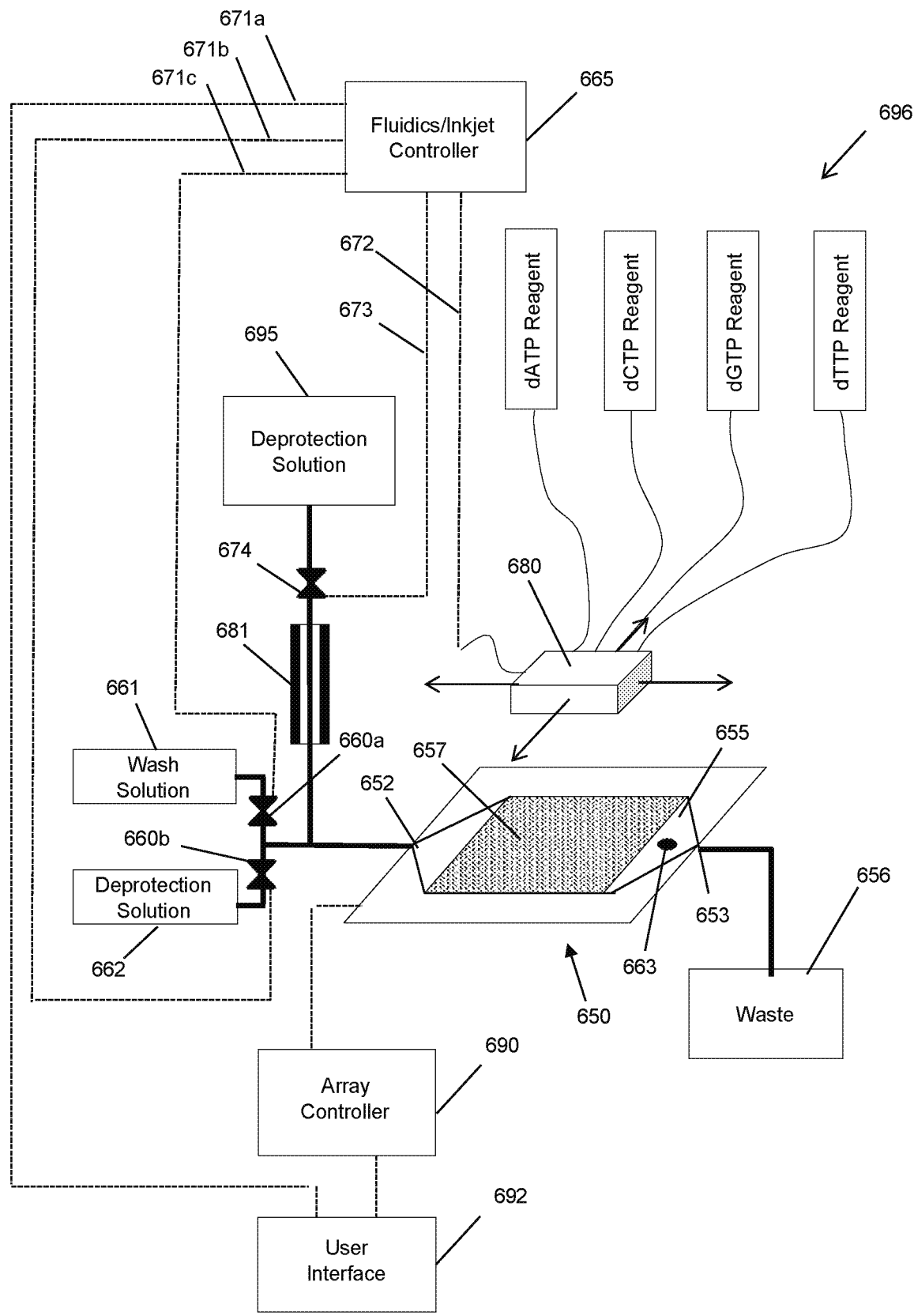
FIG. 6C illustrates diagrammatically an embodiment of an apparatus for synthesizing polynucleotides on an electrode array which uses droplet delivery of reagents to reaction sites of the electrodes.

FIG. 6C illustrates diagrammatically an alternative apparatus for implementing methods of the invention wherein some reagents are delivered to reaction sites using an inkjet droplet generator. Many of the design features described above are applicable to this embodiment. As above, flow cell and electrode array (650) comprise an array of reaction sites each of which may include a microwell, coatings to enhance attachment of initiators or other components and each of which is operationally associated with one or more electrodes. As above, in some embodiments, the electrode array may be integrated with CMOS control and measurement circuitry as a single chip. A flow cell can have a variety of designs for controlling the path and flow rate of reagents over the electrode array; however, unlike the apparatus of FIG. 6B, here reaction sites of the electrode array must be accessible for delivery of reagent-containing droplets by print head (680). In one aspect, a flow cell comprises an inlet (652), an outlet (653), and a flow chamber (655) for defining the flow path of reagents (not delivered by print head (680)) over electrode array (657). Reagents are discarded into a waste container (656) after exiting flow cell and sensor array (650). In accordance with this embodiment, a function of the apparatus is to deliver different reagents either via inlet (652) or print head (680) to flow cell and electrode array (650) in a predetermined sequence, for predetermined durations, at predetermined flow rates, and optionally to measure physical and/or chemical parameters at the electrode or reaction sites that provide information about the status of a reaction taking place therein. To this end, fluidics controller (658) controls by lines (671a, 6711b and 671c) valves (660a and 660b) and print head (680). Valves (660a) and (660b) control the delivery of wash solution (661) and deprotection solution (662) (if required) to flow cell (657). Guidance for design and control of inkjet delivery systems is well known by those with skill in the art and may be found in U.S. patent publication US2003/0170698 and U.S. Pat. Nos. 6,306,599; 6,323,043; 7,276,336; 7,534,561; and like references.

In some embodiments, a single reference electrode (608) may be positioned upstream of flow cell and sensor array (600). In other embodiments, a reference electrode may be positioned within the flow chamber. In some embodiments, a single counter electrode (663) may be employed, or in other embodiments, more than one counter electrodes may be employed, and as described, above such counter electrodes may or may not be integrated on the same electronic substrate as the working electrodes of array (657).

The apparatus is controlled through user interface (692) which, in turn, actuates and monitors synthesis steps through fluidics/inkjet controller (665) and array controller (690) as indicated by dashed lines (671, 672 and 673). In particular, physical parameters, such as temperature, and circuitry for electrode selection, voltage control, sensor readouts, and the like, are handled by array controller (690); selection of reagents (696), droplet rates, head movement, and the like, is controlled by fluidics/inkjet controller (665). In some embodiments, during droplet delivery of 3'-O-protected dNTP monomers and/or template-free polymerase, the electrolyte connect between reaction sites and reference electrode (681) is broken as flow cell (655) may be drained to prevent cross contamination between adjacent reaction sites that receive different monomers. In some embodiments, such cross contamination may be avoided by providing reaction sites surrounded by hydrophobic regions so that each site is encompassed by an isolated liquid droplet when an electrolyte, such as, a wash solution or a deprotection solution, recedes from the flow chamber, e.g. as described in Brennan, U.S. Pat. Nos. 5,474,796, 6,921,636, and the like. In particular, when the flow chamber is flooded with deprotection solution a continuous electrolyte path is restored to reference electrode (681) and counter electrode(s) which may be either on array (657) or off-array.

In some implementations, the value of the voltage difference between working electrodes and reference electrode is selected to avoid unwanted redox reactions, such as electrolysis of water, so that bubbles do not form in the fluidics of the device. In some embodiments, predetermined voltage differences to bring about electrochemical reactions in the invention are about 1.5 volts or less.

In some embodiments, methods of the invention, such as implemented by the apparatus of FIGS. 6B and 6C, may comprise the steps of (a) providing a spatially addressable array of reaction sites, wherein each reaction site is operationally associated with at least one working electrode and has disposed thereon initiators attached by their 5'-ends and having a 3'-O-electrochemically labile protecting group; (b) performing for each kind of nucleotide a cycle comprising steps of (i) deprotecting initiators or elongated fragments at electrodes at predetermined addresses by generating a voltage difference between each of the electrodes at the predetermined addresses and a reference electrode so that the electrochemically labile protecting group is cleaved, thereby generating free 3'-hydroxyls on the initiators or elongated fragments at the electrodes of the predetermined addresses, and (ii) contacting under elongation conditions the electrodes at the predetermined addresses with a 3'-O-electrochemically labile-protected nucleoside triphosphate and a template-independent DNA polymerase so that the initiators or elongated fragments at the predetermined addresses are elongated by the incorporation of a 3'-electrochemically labile-protected nucleoside triphosphate to form 3'-O-electrochemically labile-protected elongated fragments; and (c) repeating step (b) until the array of polynucleotides of predetermined sequences is completed. Reaction sites are generally discrete regions on a substrate within which a single kind of polynucleotide with a predetermined sequence is synthesized. Reaction sites are spatially addressable in the sense that they have well defined locations on a substrate or surface, which usually form a regular pattern, such as a rectilinear pattern, hexagonal pattern, or the like. Each reaction site is operationally associated with at least one working electrode in the sense that the electrical potential, or voltage, at the reaction site may be controlled or determined by its associated one or more working electrodes. Typically reaction sites and working electrodes are spatially aligned. That is, if an electrode is a disc or other planar structure embedded on a substrate surface, the area occupied by a reaction site corresponds to the area of the electrode surface. This is advantageous for ensuring a uniform electrical effect in reactions taking place at the reaction site. In some embodiments, a reaction site may comprise a substrate or film on a surface of a working electrode, for example, such substrate or film may be used to facilitate attachment and/or retention of components, such as, initiators. Such substrates and electrodes may be integrated in a semiconductor device, such as a CMOS device. In reference to step (b), performing the indicated cycle of steps for each kind of nucleotide is not intended to be limited to the four nucleotides A, C, G and T. In some embodiments, each kind of nucleotide means a subset of A, C, G and T. In other embodiments, each kind of nucleotide means an extended set that may include non-natural nucleotides or other nucleotide analogs that may be useful for encoding information in polynucleotides. A variety of template-independent DNA polymerases may be employed in methods of the invention; in particular, variants of terminal deoxynucleotidyl transferase are employed, e.g. as described in Ybert et al, International patent publication WO/2019/030149, or the like. The cycles of step (b) may include further steps, such as washing steps. Elongation conditions comprise buffers, salts, temperature, co-factors and the like, that are necessary or useful for incorporation activity of the template-free polymerase employed.

In some embodiments, an electrochemically labile protecting group may be pH sensitive and pH may be regulated by voltage difference between working electrodes and a reference electrode which voltage activates an electroactive agent which, in turn, changes the pH, e.g. Southern, U.S. Pat. No. 5,667,667; Mauer et al, U.S. Pat. No. 9,267,213; and the like, which are hereby incorporated by reference. Exemplary, electroactive agents include hydroquinone, benzoquinone, quinone, and derivatives thereof.

In some embodiments, electrochemically labile protecting groups may themselves be redox sensitive such that a voltage difference between a working electrode and a reference electrode converts the electrochemically labile protecting group into a reduced state thereby cleaving said electrochemically labile protecting group. In particular, in some embodiments, a redox sensitive 3'-O-protection group is azidomethyl.

The apparatus described above, or like apparatus, may be used to store and retrieve information encoded in the synthesized polynucleotides. Information encoded in the polynucleotides may be retrieved by sequencing the polynucleotides. Virtually any nucleic acid sequencing technique may be used, but for some embodiments, particularly those in which sequencing take place on an electrode array, sequencing-by-synthesis techniques are of primary interest, for example, as disclosed in Bentley et al, Nature, 456: 53-59 (2008); Rothberg et al, Nature, 475: 348-352 (2011); Ravi et al, Methods Mol Biol. 1706: 223-232 (2018); and the like. In some embodiments, polynucleotides on an electrode array of the invention are sequenced or read using a sequence-by-synthesis approach that employs reversible terminators, such as, reversible terminators carrying cleavable fluorescent labels. Such sequencing methods are described in the following references, which are incorporated herein by reference: Wu et al, Proc. Natl. Acad. Sci., 104(42): 16462-16467 (2007); Guo et al, Acc. Chem. Res. 43(4): 551-563 (2010); Ju et al, Proc. Natl. Acad. Sci., 103(52): 19635-19640 (2006); Guo et al, Proc. Natl. Acad. Sci., 105(27): 9145-9150 (2008); Barnes et al, U.S. Pat. No. 7,057,026; and the like. In particular, in some embodiments, reversible terminators with fluorescently labeled 3'-O-azidomethyl nucleoside triphosphates are employed in the sequencing by synthesis method for sequencing polynucleotides on electrode arrays of the invention. In some embodiments, incorporated 3'-O-azidomethyl nucleotides are de-blocked electrochemically after a fluorescence measurement is made to determine the identity of the complementary nucleotide in the polynucleotide template.

In some embodiments, methods for storing information in polynucleotides and retrieving information from such polynucleotides may comprise the following steps: (a) providing a spatially addressable array of reaction sites, wherein each reaction site is operationally associated with at least one working electrode and has disposed thereon initiators attached by their 5'-ends and having a 3'-O-electrochemically labile protecting group; (b) performing for each kind of nucleotide a cycle of (i) deprotecting initiators or elongated fragments at electrodes at predetermined addresses by generating a predetermined voltage difference between each of the electrodes at the predetermined addresses and a reference electrode so that the electrochemically labile protecting group is cleaved, thereby generating free 3'-hydroxyls on the initiators or elongated fragments at the electrodes at the predetermined addresses, (ii) contacting under elongation conditions the electrodes at the predetermined addresses with a 3'-O-electrochemically labile-protected nucleoside triphosphate and a template-independent DNA polymerase so that the initiators or elongated fragments at the predetermined addresses are elongated by the incorporation of a 3'-electrochemically labile-protected nucleoside triphosphate to form 3'-O-electrochemically labile-protected elongated fragments; (c) repeating step (b) until the array of polynucleotides of predetermined sequences is completed, wherein each of the completed polynucleotides comprises in a 5' to 3' direction an information encoding region and a sequencing primer binding site at its 3' end; and (d) retrieving information from the information encoding region by annealing a sequencing primer to the sequencing primer binding site and sequencing by synthesis the information encoding region of the completed polynucleotides at one or more reaction sites. In some embodiments, the information encoding region may contain other features, such as, additional primer binding sites, restriction sites, or the like, for processing or manipulating the polynucleotides.

In some embodiments, sequencing by synthesis may comprise incorporating a labeled reversibly blocked nucleoside triphosphate into said sequencing primer or an extension thereof by a template-dependent polymerase such that the identity of the incorporated labeled reversibly blocked nucleoside triphosphate is determined by said sequence of the polynucleotide at the reaction site. In some embodiments, the label and the blocking group of the labeled reversibly blocked nucleoside triphosphate may be attached to separate moieties of the labeled reversibly blocked nucleoside triphosphate, so that de-blocking and label removal may be accomplished by the same step or by different steps. Of particular interest are labeled reversibly blocked nucleoside triphosphate that comprise a 3'-O-electrochemically labile blocking group that is removed from the extended sequencing primers at reaction sites of predetermined addresses by generating a predetermined voltage difference between each of the electrodes at the predetermined addresses and a reference electrode. In this manner, polynucleotides at all or a predetermined subset of reaction sites may be sequenced, or read.

It is understood that the voltage differences employed to cleave the different protection or blocking groups may be different, so that reference to "a predetermined voltage difference" means a predetermined voltage difference specific for bringing about a specific effect, such as, a desired local pH change via an electroactive agent to bring about cleavage of a specific group, or direct cleavage of a specific group by its reduction, or the like.

In some embodiments it may be advantageous to synthesize polynucleotides in low quantities at discrete reaction sites then amplify them to further populate, or fill in, the reaction sites. This may be accomplished by techniques depending on thermal cycling, such as bridge PCR, or it may be accomplished by isothermal techniques, such as template walking of recombinase-polymerase amplification.

In some embodiments, either a portion of reaction sites on an array may have initiators with orthogonal 3'-O-electrochemically labile protection groups to the protection groups on initiators of the other reaction sites, or a portion of initiators within the same reaction site may comprise orthogonal 3'-O-electrochemically labile protection groups with respect to the other initiators at the same reaction site. By "orthogonal" in reference to two or more protection groups it is meant that conditions used to cleave one protection group will not affect the other protection groups, and vice versa for the conditions of removal for each protection group.

In some embodiments, at least two completed polynucleotides at different reaction sites have sequencing primer binding sites comprising different sequences, so that the at least two completed polynucleotides can be sequenced separately. In some cases, sequencing primer binding sites are attached by template-free enzymatic synthesis, in other embodiments, such primer binding sites may be ligated to synthesized polynucleotides.

In some embodiments, the different sequences of the sequencing primer binding sites are associated with different information encoded in their corresponding information encoding regions. Such different sequencing primer binding sites can index subsets of information stored in the polynucleotides of an array.

Figure 7A:
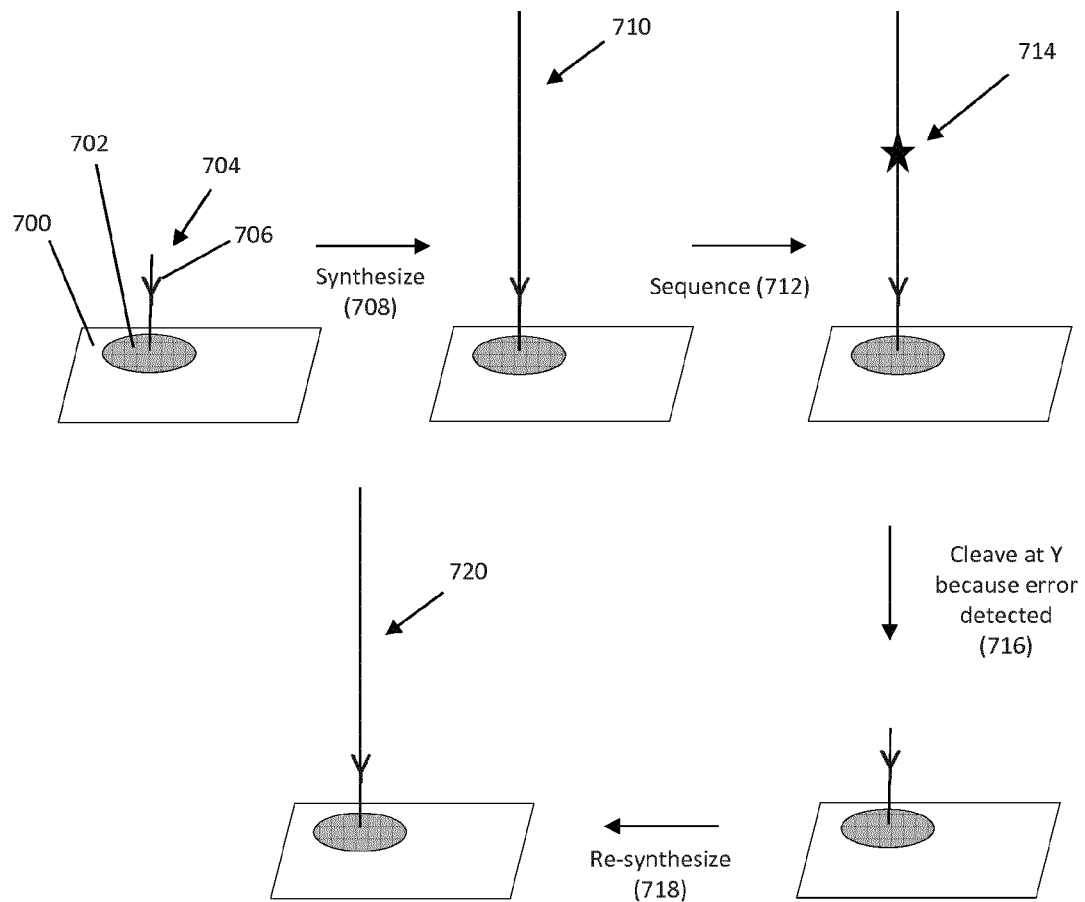

FIGS. 7A-7D describe various embodiments of the invention for producing, reducing error in, storing and retrieving information from, polynucleotides whose nucleotide sequences encode information. FIG. 7A illustrates an embodiment that includes error correction. Electrode array (700) is shown with single reaction site (702) associated with an electrode (not shown) and initiator sequence (704) having a free 3'-hydroxyl and a labile bond or nucleotide (706) that is capable of being cleaved to leave a free 3'-hydroxyl. In some embodiments, bond or nucleotide (706) is electrochemically labile such that it may be selectively cleaved at reaction site (702). Initiator (704) is elongated (708) by template-free enzymatic synthesis using 3'-O-electrochemically labile-protected nucleoside triphosphate and a template-independent DNA polymerase to produce full length polynucleotide (710), after which full length polynucleotide (710) is sequenced to confirm that it has the desired sequence. If error (714) is determined, then polynucleotide (710) may be selectively cleaved at labile bond Y (706) and a replacement polynucleotide (720) may be re-synthesized (718).

In some embodiments, steps of synthesis may be monitored by detecting labeled pyrophosphate groups that are released from the dNTPs during incorporation, e.g. Fuller et al, U.S. Pat. No. 7,223,541, so that (for example) a profile of fluorescent signals from a reaction site will indicate whether the intended nucleotide was incorporated into the growing polynucleotide and the extent of mis-incorporation, if any.

Figure 7B:
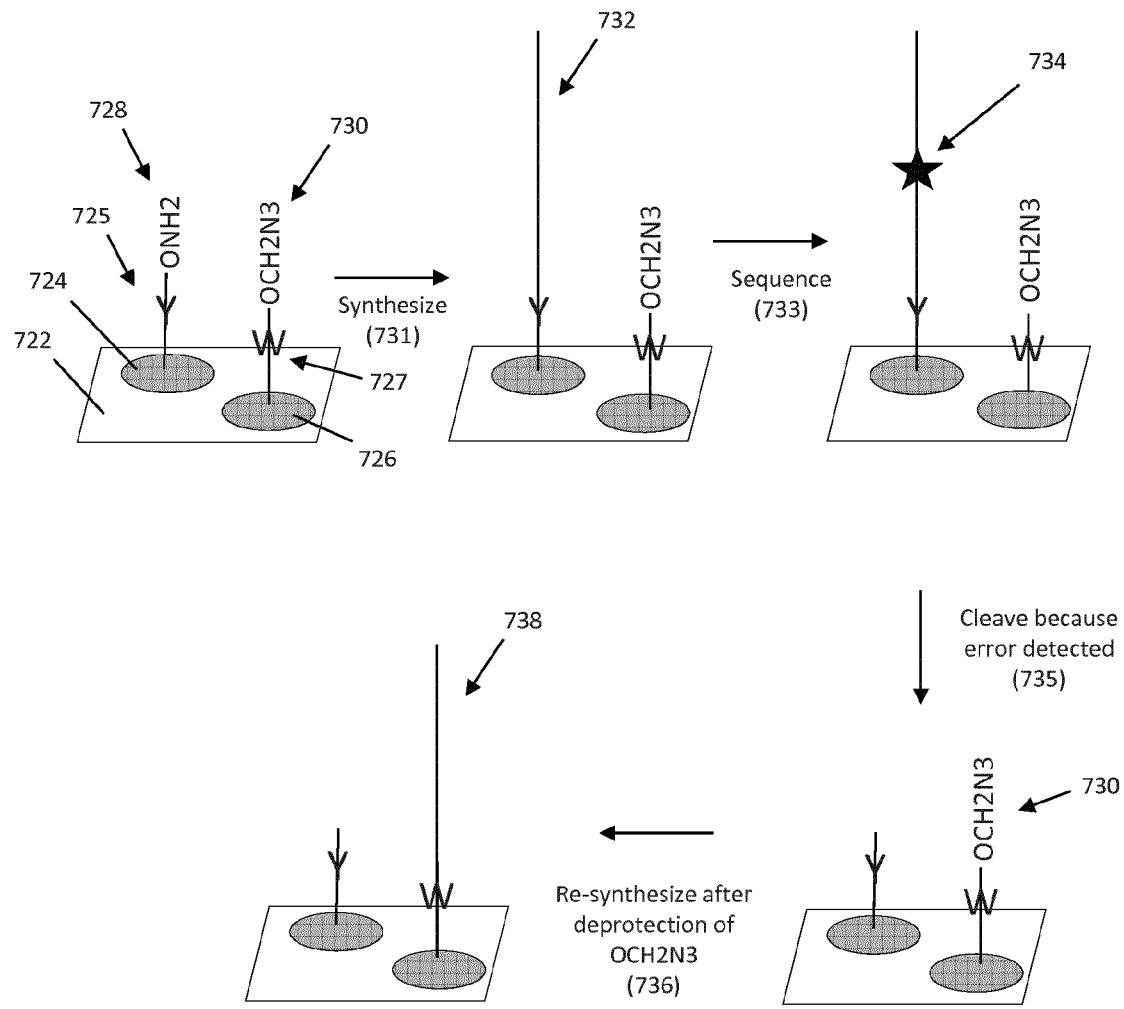

FIG. 7B illustrates another embodiment of the invention in which different reaction sites of an electrode array have initiators with orthogonal protection groups. In one application of this embodiment, polynucleotides may be synthesized on only a portion of the reaction sites by deprotecting only first protection groups on initiators at a portion of reaction sites, wherein second protection groups at the other reaction site are not removed. In alternative embodiments, the initiators with orthogonal protection groups may populate the same reaction site. As shown in FIG. 7B, electrode array (722) has reaction sites (724) and (726) each with initiators (725) and (727), respectively. Initiators (725) and (727) optionally include labile bonds "Y" and "W", respectively, and electrochemically labile protection groups, 3'-O—NH2 (728) and 3'-O—CH2N3 (730), respectively. One of the protection groups, for example, 3'-O—NH2, may be removed and polynucleotide (732) synthesized (731). If upon sequencing (733) polynucleotide (732) error (734) is discovered, then the polynucleotide with the incorrect sequence optionally may be cleaved (735), second protection group (730) at a different reaction site may be deprotected and a polynucleotide with the intended sequence may be re-synthesized (736) to produce correct sequence polynucleotide (738). Alternatively, polynucleotide (732) with error (734) may be left intact on array (722), that is, not cleaved, and its address or position annotated as containing an incorrect sequence. The error-correction schemes of FIGS. 7A-7B may be used with encoding schemes that rely on redundancy or they may be used to reduce the amount of redundancy required to ensure a predetermined level of reliability of stored information.

Embodiments of FIGS. 7A and 7B may be implemented with the following steps: (a) providing a spatially addressable array of reaction sites, wherein each reaction site is operationally associated with at least one working electrode and has disposed thereon initiators attached by their 5'-ends and having a 3'-O-electrochemically labile protecting group; (b) performing for each kind of nucleotide a cycle of (i) deprotecting initiators or elongated fragments at electrodes at predetermined addresses by generating a predetermined voltage difference between each of the electrodes at the predetermined addresses and a reference electrode so that the electrochemically labile protecting group is cleaved, thereby generating free 3'-hydroxyls on the initiators or elongated fragments at the electrodes at the predetermined addresses, (ii) contacting under elongation conditions the electrodes at the predetermined addresses with a 3'-O-electrochemically labile-protected nucleoside triphosphate and a template-independent DNA polymerase so that the initiators or elongated fragments at the predetermined addresses are elongated by the incorporation of a 3'-electrochemically labile-protected nucleoside triphosphate to form 3'-O-electrochemically labile-protected elongated fragments; (c) repeating step (b) until the array of polynucleotides of predetermined sequences is completed, wherein each of the completed polynucleotides comprises in a 5' to 3' direction an information encoding region and a sequencing primer binding site at its 3' end; and (d) retrieving information from the information encoding region by annealing a sequencing primer to the sequencing primer binding site and sequencing by synthesis the completed polynucleotides at one or more reaction sites. In some embodiments, each initiator comprises a cleavable nucleotide or cleavable bond such that an initiator can be cleaved at the cleavable nucleotide or cleavable bond whenever said retrieved information indicates a synthesis error. After such cleavage the polynucleotide may be re-synthesized from the cleaved initiator. In some embodiments, such cleavable bonds or nucleotides are electrochemically labile. In other embodiments, a portion of the reaction sites of an array comprise initiators with orthogonal 3'-O-electrochemically labile protection groups with respect to other 3'-O-electrochemically labile protection groups of initiators of other reaction sites on the array. In such embodiments, methods further includes the steps of deprotecting initiators at at least one reaction site having initiators with orthogonal 3'-O-electrochemically labile protection groups and re-synthesizing the polynucleotide of the predetermined sequence whenever said retrieved information indicates a synthesis error. That is, whenever sequencing indicates an error, a polynucleotide with the desired correct sequence is re-synthesized on one of reaction sites of the portion of reaction site containing initiators with orthogonal protection groups. The polynucleotide with the incorrect sequence may be cleaved or it may be noted as having an incorrect sequence, but otherwise not cleaved from the array.

In some embodiments, synthesized polynucleotides are stored on the electrode arrays; that is, after synthesis the polynucleotides remain on the array and are stored along with the array. Information encoded in the polynucleotides may be retrieved by either sequencing the polynucleotides in situ while they remain on the array or they may be cleaved from the array and sequenced.

FIG. 7C illustrates three schemes for reading, or sequencing, polynucleotides on electrode array (740) with reaction sites (741). In scheme 1, after information encoding section (742) is synthesized, a self-complementary hairpin-forming section (744) is synthesized comprising sequence X (746), loop sequence (748), and sequence Z (750), the complement of sequence X (746). Under annealing conditions, Z (750) hybridizes to (746) so that sequencing reactions (752) can be performed to produce extended strand (754). As mentioned above, the resulting double stranded polynucleotide may be stored as is, or it may be cleaved from array (740) for separate storage. In some embodiments, the resulting double stranded polynucleotide may in a retrieval process be cleaved at hairpin (744) in order to separate complementary strand (754) produced in the sequencing reaction, for example, if the sequencing reaction leaves undesirable adducts. Scheme 1 has the advantage that the lack of readily accessible free 3' or 5' hydroxyl makes the resultant double stranded polynucleotide more resistant to nuclease digestion. Scheme 1 has the advantages of (i) not requiring a sequencing primer, and (ii) separate reading at any reaction site is possible if site-specific primers are selected or if electrochemically labile block groups are used in the sequencing chemistry. Scheme 2 is similar to scheme 1 except instead of hairpin (744), polynucleotide (755) is appended with primer binding site (756). Primer (760) is annealed to primer binding site (756) and a sequencing reaction is performed to read the sequence of polynucleotide (755). Scheme 2 has the advantage that repeat reads are possible on-array. Also, separate reading at any reaction site is possible if site-specific primers are selected or if electrochemically labile block groups are used in the sequencing chemistry.

In scheme 3, after synthesis of polynucleotide (765) on initiator containing cleavable bond (766), polynucleotide (765) is cleaved (768) to release strand (770) which may be stored separately from array (740).

Figure 7D:
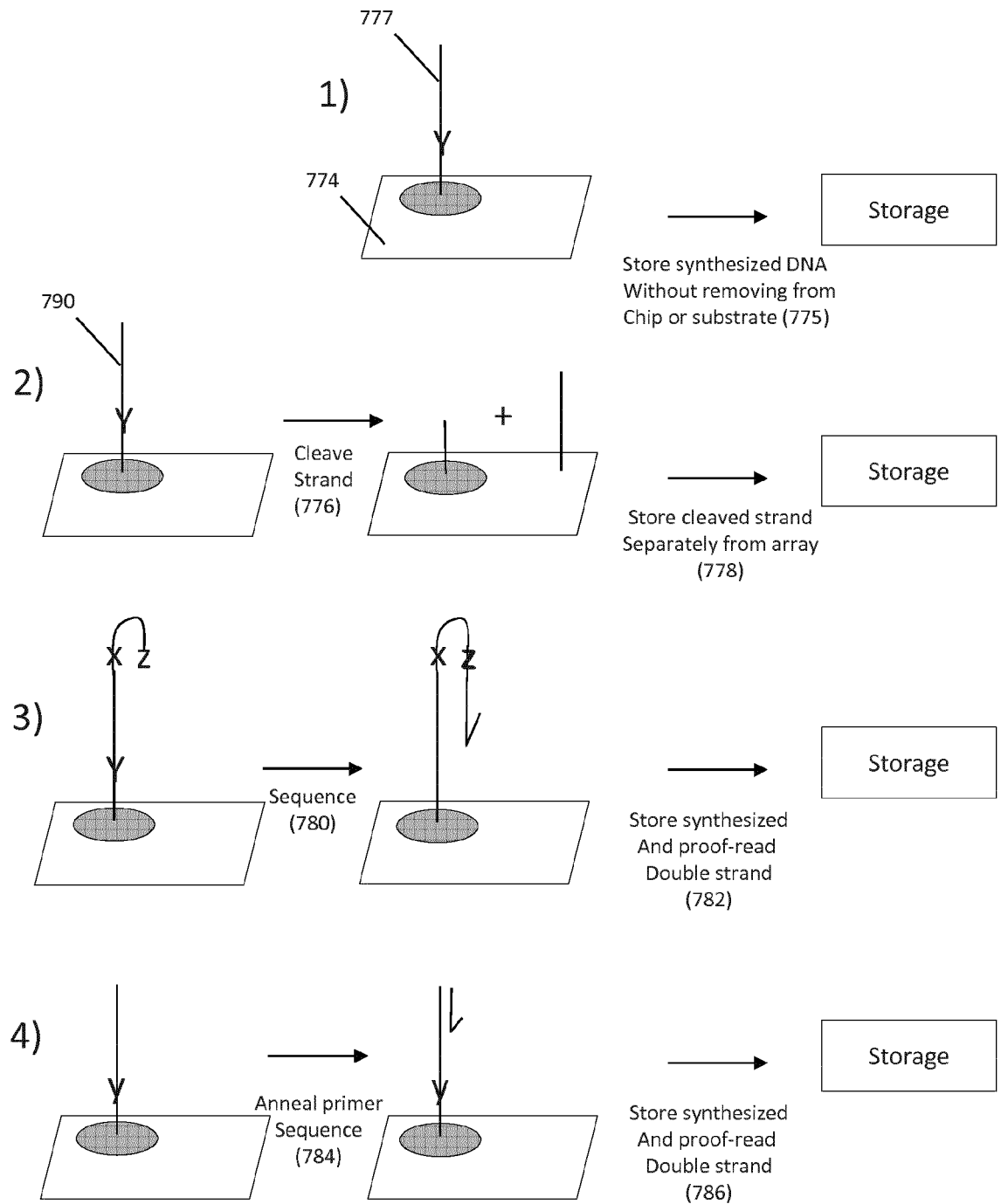

FIG. 7D reviews configurations for polynucleotide storage. Panel 1) shows the simplest storage configuration; namely, after polynucleotides (777) is synthesized on array (774), both the array and polynucleotide are stored together without cleavage of polynucleotide (777). The configuration of panel 2) is similar to that of panel 1) except that after synthesis polynucleotide (790) is cleaved (776) and stored without the array. The configurations of panels 3) and 4) correspond to synthesis schemes 1 and 2, respectively. Both configuration result in double stranded polynucleotides which have the advantage of permitting the strands to be stored separately for increased security of the encoded information.

C. Other Synthesis Considerations.

Error Correction Process. The biggest source of errors anticipated is depurination. This degradation of DNA bases in acidic conditions leaves an abasic site in the DNA strand. When sequenced, they appear as a mix of 4 bases with SBS and are difficult to handle. A glycosylase enzyme can be used to cleave the oligonucleotides at those abasic sites, making them undetectable to sequencing (no sequencing primer) so they won't pollute the data.

Reset synthesis. If fragments above 500 nt are synthesized, the use of SBS may be insufficient for their sequencing. It is thus an object of the present invention to provide a new method of sequencing long fragments, and particularly fragments above 500 nt. To this end, the invention proposes to add one or several intermediary sequencing primers within the oligonucleotide to enable sequencing successive shorter oligonucleotides.

As illustrated in FIG. 2, the "Data" of the oligonucleotide fragment can be fragmented into several sub-data fragments ("Data 1" and "Data 2" in FIG. 2). When sequenced, this oligonucleotide can be sequenced first using Antisense sequencing primer and Forward sequencing primer 1 with dual paired ends (300 nt read—Data 1, Random access ID, address), and then using Forward sequencing primer 2 (150 nt—Data 2). This can be used with several intermediary forward primers to read any sequence needed. To synthesize those oligonucleotides on chip, it is possible to either synthesize the intermediary primers one nucleotide by one nucleotide or use a ligation enzyme. The error pattern after the intermediary primer is exactly the same as before.

To enable reset synthesis, the present invention also provides specific dUTP-ONH2 reversible terminator nucleotides or rUTP-ONH2 reversible terminator nucleotides. The present invention also provides enzymes variants able to incorporate at acceptable yield those 2 nucleotides (see for instance WO2017/216472). The dUTP-ONH2 may be cleaved via the action of a USER enzyme mix: uracil DNA glycosylase and endonuclease VIII during 15 min; and the rUTP-ONH2 via the action of KOH 1M for 2 hours. As a result, it is possible to incorporate those nucleotides at any position in the sequence of the oligonucleotide and particularly between the data sections and the sequencing primer sections and release the different part of the data to create individual oligonucleotides from one single synthesis site.

Oligo pool creation. After synthesis, it is possible to get the library synthesized in the form of an oligo pool. There are two possibilities to get this pool:
Cleave the oligonucleotides
Perform an isothermal amplification on chip
The second solution gives the possibility to keep the DNA material on chip to ease sequencing.

As described below, the oligonucleotides may have sequencing primers on their 5' and 3' end. Isothermal amplification of this library thanks to these primers is envisioned. Isothermal amplification is preferred to standard PCR because cycling temperature can be damaging for the chip.

D. Nucleic Array Synthesis Compatible with Sequencing Workflow

In a another aspect, the invention provides new nucleic array synthesis that is compatible with sequencing workflow.

It is very tedious to synthesize DNA and to sequence it afterward because the chemistry used for reading and writing are not compatible. Synthesis and sequencing have never been performed in the same instrument because they involve two very different technologies (organic chemistry for synthesis and enzymatic reactions for sequencing). For instance, phosphoramidite reagents used for phosphoramidite chemistry must be manipulated in an anhydrous media (very low traces of water will prevent the reaction from happening efficiently) whereas sequencing is performed in aqeuous solutions in the case of Sequencing by synthesis, pyrosequencing, nanopore sequencing and ion semiconductor sequencing among others. For the industry this is a challenge because there is a need to verify the sequence of DNA synthesized before use. It is especially true when DNA/RNA is synthesized on chips (microarray industry or for synthesis of oligo pools).

On chip synthesis compatible with sequencing. The present invention provides a solution to the above problem by allowing on chip synthesis compatible with sequencing. According to the present invention, the DNA/RNA synthesis is performed enzymatically on flow-cells compatible with sequencing instruments. Because sequencing relies on enzymatic synthesis of a strand of DNA complementary to the strand to sequence in pyrosequencing, sequencing by synthesis and ion semiconductor sequencing, the flow cells are optimized for enzymatic synthesis, with the following aspects:

1. Possibility to inject aqueous reagents
2. Laminar flows in the chip
3. Passivation of surface to prevent DNA, enzyme and nucleotide sticking
4. Stable for multiple enzymatic cycles DNA synthesis can be performed for instance using electrochemistry, inkjet printing or photoinduced deprotection. After synthesis, the product obtained can be array with a wide variety of oligonucleotides on its surface, each spot containing a different oligonucleotide. This configuration is exactly the one used for sequencing by synthesis. Each spot is a sequencing cluster. Adding a sequencing primer by synthesis or ligation on the 3' is the only preparation required before sequencing. Usually, sample preparation is way more complex, with several steps (dilution, ligation, PCR, bridge amplification, etc.). It can also be an array with microbeads into microwells, each microbead having oligonucleotides of a defined sequence on their surface. The instrument could even be the same for synthesis and sequencing. Photochemical synthesis and sequencing by synthesis for example could be performed in a similar instrument as they both rely on optics and need a transparent flow cell. Electrochemical synthesis and ion semiconductor (Ion Torrent) sequencing for instance also are particularly compatible.

E. Combinatorial Encoding Scheme for DNA Data Storage.

In a further aspect, the present invention provides encoding scheme for DNA data storage. DNA data storage has the potential to disrupt the data storage market thanks to very high data density, easy and long-term storage. It thus requires very high DNA synthesis and sequencing throughput to be viable. DNA synthesis is usually performed on 2D microarray. Digital data is usually stored in base 2, and DNA is in base 4 (2 bits could theoretically be encoded in one nucleotide). One solution to increase data density (and incidentally synthesis and sequencing throughput) is to increase this encoding base further than 4. One solution has been to add unnatural DNA bases (for instance Steven Benner's AEGIS nucleotides) but it is limited and it can make sequencing harder. The present invention now proposes to increase the encoding base using only the four natural bases. This scheme could also be implemented with additional unnatural nucleotides.

Figure 4:
FIG. 4 presents an example of encoding using the absence/presence combinatorial scheme of the invention, as presented in FIG. 3 on one well of a DNA array. The data is encoded in base 14 (X1, X2, . . . , X14). The code X1 X2 X10 X6 X11 X8 represented here is stored on 6 nt long DNA strands. It encodes more than 22 bits of data. A 12 nucleotide DNA fragment would have been needed to store the same amount of data using quaternary encoding.

Combinatorial schemes. To further implement data density, the invention proposes is to implement a combinatorial scheme by adding mixes of nucleotides at each cycle instead of only one of the four nucleotides (FIGS. 3 and 4). On one well, adding a mix of nucleotide per cycle can increase the base in which the data are encoding. Using the presence/absence mechanism described above, the encoding base is 14 and it is possible to increase the data density by approximately 2. Using the 25% combinatorial scheme (FIG. 3), the base is 35 enabling the encoding of 5 bits per cycle ($35>32=2^{\rightarrow}5$). A 10% combinatorial scheme with 10 levels (X1=AAAAAAAAAA, X2=AAAAAAAAAT, etc) would give a 268 base. This kind of combinatorial encoding can be rather easily sequenced using SBS technology and quantifying the quantity of nucleotide on each spot.

| Encoding method | Number of bits per cycle |
| --- | --- |
| Quaternary | 2 |
| Presence/absence combinatorial | $Ln(14)/ln(2) = 3.81$ |
| 25% combinatorial | $Ln(35)/ln(2) = 5.13$ |
| 10% combinatorial | $Ln(268)/ln(2) = 8.07$ |

Figure 5:
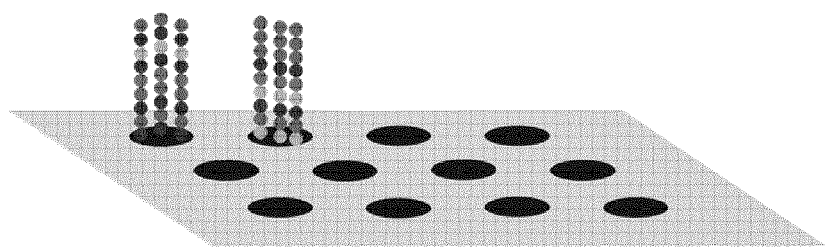
FIG. 5 illustrate an example of pseudo 3D DNA data storage. The microarray grid is in 2D and the DNA sequence (or mix of sequence in the combinatorial scheme) is the $3^{rd}$ dimension.

Pseudo 3D data storage. This scheme can be used to increase data density when the synthesis support is stored (to be sequenced in the future if data needs to be retrieved). Keeping the synthesis support dramatically reduces the number of reads required to decipher a defined amount of data in sequencing. Indeed, when data is stored in DNA oligo pools, each fragment needs to be read an average of 50 times (read depth of 50) to be sure that every oligonucleotide has been sequenced. When the solid support is kept, the read depth is 1 as oligonucleotides are perfectly ordered. In the context of the present invention, this is named pseudo 3D data storage (Flow cell is 2D and the sequence of nucleotide represents the $3^{rd}$ dimension) to enable the use of DNA data storage for medium cold data storage and enable the easy readout of the digital data (FIG. 5). With 1 µm² wells, 400mers, and 25% combinatorial scheme, the data density would be more than 2 kbit per µm² on our flow cells. This data density compares with the densest data storage media today:

Magnetic tape: 200 GB/in² (Sony world record in 2017)= 2480 bits/µm²

HD Bluray disc: 13.6 GB/in² (4 layers blu ray)=215 bits/µm²

1 µm², 400mers, 25% combinatorial: >2000 bits/µm²

Using 10% combinatorial scheme would enable to achieve more than 3.5 kbits/µm² which is out of reach today. If synthesis is performed in 1 µm beads instead of chips, one may have more than 100 TB of data in 1 cm^3 which exceeds current storage technologies by far. Beads could be redeposited in sequencing chip for readout with read depth of 1.

The synthesis and sequencing methods of the invention may be used with virtually any coding scheme, such as those disclosed in the following references, which are incorporated by reference: Bornholt et al, IEEE Micro, 37(3): 98-104 (2017); Goldman et al, Nature, 494: 77-80 (2013); Chen et al, U.S. patent publication US2018/0265921; Chen et al, US20180230509A1; Strauss et al, US20170141793A1; Blawat et al, EP3067809A1; and the like.

Cleavable Linkages and Nucleotides

A wide variety of cleavable linkages, or more particularly, cleavable nucleotides, may be used with embodiments of the invention. As used herein, the term "cleavable site" refers to a nucleotide or backbone linkage of a single stranded nucleic acid sequence that can be excised or cleaved under predetermined conditions, thereby separating the single stranded nucleic acid sequence into two parts. In some embodiments, a step of cleaving a cleavable nucleotide, a cleavable linkage or cleavable bond leaves a free 3'-hydroxyl on a cleaved strand, thereby, for example permitting the cleaved strand to be extended by a polymerase. Cleaving steps may be carried out chemically, thermally, enzymatically or by light-based cleavage. In some embodiments, cleavable nucleotides may be nucleotide analogs such as deoxyuridine or 8-oxo-deoxyguanosine that are recognized by specific glycosylases (e.g. uracil deoxyglycosylase followed by endonuclease VIII, and 8-oxoguanine DNA glycosylase, respectively). In some embodiments, cleavage by glycosylases and/or endonucleases may require a double stranded DNA substrate.

In some embodiments, cleavable nucleotides include nucleotides comprising base analogs cleavable by endonuclease III which include, but are not limited to, urea, thymine glycol, methyl tartonyl urea, alloxan, uracil glycol, 6-hydroxy-5,6-dihydrocytosine, 5-hydroxyhydantoin, 5-hydroxycytocine, trans-1-carbamoyl-2-oxo-4,5-dihydrooxy-imidazolidine, 5,6-dihydrouracil, 5-hydroxycytosine, 5-hydroxyuracil, 5-hydroxy-6-hydrouracil, 5-hydroxy-6-hydrothymine, 5,6-dihydrothymine. In some embodiments, cleavable nucleotides include nucleotides comprising base analogs cleavable by formamidopyrimidine DNA glycosylase which include, but are not limited to, 7,8-dihydro-8-oxoguanine, 7,8-dihydro-8-oxoinosine, 7,8-dihydro-8-oxoadenine, 7,8-dihydro-8-oxonebularine, 4,6-diamino-5-formamidopyrimidine, 2,6-diamino-4-hydroxy-5-formamidopyrimidine, 2,6-diamino-4-hydroxy-5-N-methylformamidopyrimidine, 5-hydroxycytosine, 5-hydroxyuracil. In some embodiments, cleavable nucleotides include nucleotides comprising base analogs cleavable by hNeil 1 which include, but are not limited to, guanidinohydantoin, spiroiminodihydantoin, 5-hydroxyuracil, thymine glycol. In some embodiments, cleavable nucleotides include nucleotides comprising base analogs cleavable by thymine DNA glycosylase which include, but are not limited to, 5-formylcytosine and 5-carboxycytosine. In some embodiments, cleavable nucleotides include nucleotides comprising base analogs cleavable by human alkyladenine DNA glycosylase which include, but are not limited to, 3-methyladenine, 3-methylguanine, 7-methylguanine, 7-(2-chloroehyl)-guanine, 7-(2-hydroxyethyl)-guanine, 7-(2-ethoxyethyl)-guanine, 1,2-bis-(7-guanyl)ethane, 1,$N^6$-ethenoadenine, 1,$N^2$-ethenoguanine, $N^2$,3-ethenoguanine, $N^2$,3-ethanoguanine, 5-formyluracil, 5-hydroxymethyluracil, hypoxanthine. In some embodiments, cleavable nucleotides include 5-methylcytosine cleavable by 5-methylcytosine DNA glycosylase.

Exemplary chemically cleavable internucleotide linkages for use in the methods described herein include, for example, -cyano ether, 5'-deoxy-5'-aminocarbamate, 3'deoxy-3'-aminocarbamate, urea, 2'cyano-3',5'-phosphodiester, 3'-(S)-phosphorothioate, 5'-(S)-phosphorothioate, 3'-(N)-phosphoramidate, 5'-(N)-phosphoramidate, -amino amide, vicinal diol, ribonucleoside insertion, 2'-amino-3',5'-phosphodiester, allylic sulfoxide, ester, silyl ether, dithioacetal, 5'-thio-furmal, -hydroxy-methyl-phosphonic bisamide, acetal, 3'-thio-furmal, methylphosphonate and phosphotriester. Internucleoside silyl groups such as trialkylsilyl ether and dialkoxysilane are cleaved by treatment with fluoride ion. Base-cleavable sites include -cyano ether, 5'-deoxy-5'-aminocarbamate, 3'-deoxy-3'-aminocarbamate, urea, 2'-cyano-3',5'-phosphodiester, 2'-amino-3',5'-phosphodiester, ester and ribose. Thio-containing internucleotide bonds such as 3'-(S)-phosphorothioate and 5'-(S)-phosphorothioate are cleaved by treatment with silver nitrate or mercuric chloride. Acid cleavable sites include 3'-(N)-phosphoramidate, 5'-(N)-phosphoramidate, dithioacetal, acetal and phosphonic bisamide. An -aminoamide internucleotide bond is cleavable by treatment with isothiocyanate, and titanium may be used to cleave a 2'-amino-3',5'-phosphodiester-O-ortho-benzyl internucleotide bond. Vicinal diol linkages are cleavable by treatment with periodate. Thermally cleavable groups include allylic sulfoxide and cyclohexene while photo-labile linkages include nitrobenzylether and thymidine dimer. Methods synthesizing and cleaving nucleic acids containing chemically cleavable, thermally cleavable, and photo-labile groups are described for example, in U.S. Pat. No. 5,700,642.

Further cleavable linkages are disclosed in the following references: Pon, R., Methods Mol. Biol. 20:465-496 (1993); Verma et al., Ann. Rev. Biochem. 67:99-134 (1998); U.S. Pat. Nos. 5,739,386, 5,700,642 and 5,830,655; and U.S. Patent Publication Nos. 2003/0186226 and 2004/0106728, Urdea et al, U.S. Pat. No. 5,367,066.

The cleavable site may be located along the oligonucleotide backbone, for example, a modified 3'-5' internucleotide linkage in place of one of the phosphodiester groups, such as ribose, dialkoxysilane, phosphorothioate, and phosphoramidate internucleotide linkage. The cleavable oligonucleotide analogs may also include a substituent on, or replacement of, one of the bases or sugars, such as 7-deazaguanosine, 5-methylcytosine, inosine, uridine, and the like.

Synthesis and cleavage conditions of chemically cleavable oligonucleotides are described in U.S. Pat. Nos. 5,700,642 and 5,830,655. Phosphorothioate internucleotide linkage may be selectively cleaved under mild oxidative conditions. Selective cleavage of the phosphoramidate bond may be carried out under mild acid conditions, such as 80% acetic acid. Selective cleavage of ribose may be carried out by treatment with dilute ammonium hydroxide. In another embodiment, a cleavable linking moiety may be an amino linker. The resulting oligonucleotides bound to the linker via a phosphoramidite linkage may be cleaved with 80% acetic acid yielding a 3'-phosphorylated oligonucleotide, which may (if desired) be removed by a phosphatase.

In some embodiments, the cleavable linking moiety may be a photocleavable linker, such as an ortho-nitrobenzyl photocleavable linker. Synthesis and cleavage conditions of photolabile oligonucleotides on solid supports are described, for example, in Venkatesan et al., J. Org. Chem. 61:525-529 (1996), Kahl et al., J. Org. Chem. 64:507-510 (1999), Kahl et al., J. Org. Chem. 63:4870-4871 (1998), Greenberg et al., J. Org. Chem. 59:746-753 (1994), Holmes et al., J. Org. Chem. 62:2370-2380 (1997), and U.S. Pat. No. 5,739,386. Ortho-nitrobenzyl-based linkers, such as hydroxymethyl, hydroxyethyl, and Fmoc-aminoethyl carboxylic acid linkers, may also be obtained commercially.

In some embodiments, ribonucleotides may be employed as cleavable nucleotides, wherein a cleavage step may be implemented using a ribonuclease, such as RNase H. In other embodiments, cleavage steps may be carried out by treatment with a nickase.

Example 1

Electrochemical Reduction of 3'-O-Azidomethyl-Nucleotide

In this example, conditions for the reduction of 3'-O-azidomethylnucleotides are determined by applying different voltages across electrodes in microwells for different lengths of time. The treated nucleotides were analyzed by LCMS and gel electrophoresis to determine reaction products.

Figure 8:
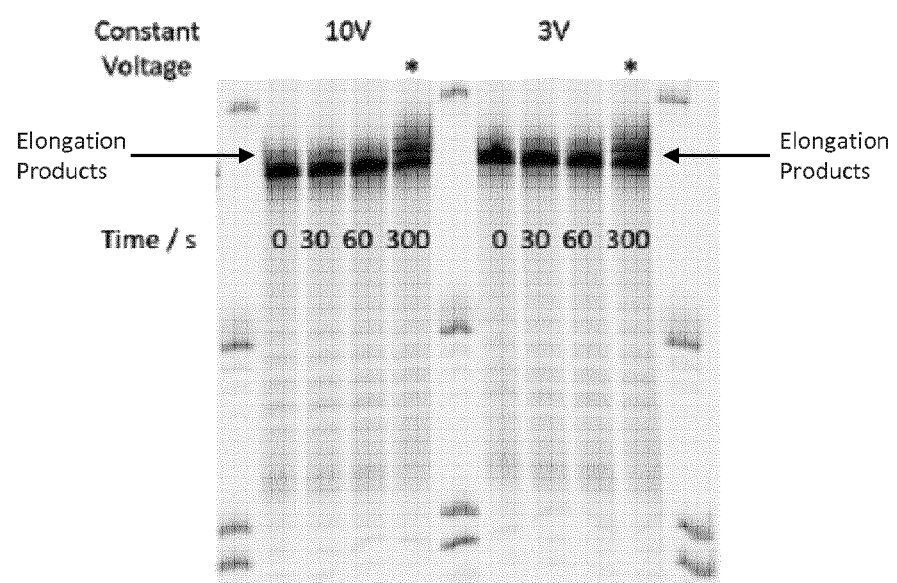
FIG. 8 shows an electropherogram of extension products from a reaction in which a mutant TdT that cannot incorporate 3'-O-azidomethyl-protected dNTPs successfully extended primers with 3'-O-hydroxyl dNTP which, in turn, were products from an electrochemically deprotection reaction, thereby demonstrating the possibility of electrochemically deprotecting 3'-O-azidomethyl-nucleotides.

Two platinum electrodes were used to apply current to 20 uL aqueous samples (@ 9 mM) of 3'-O-azidomethyldeoxythymidine under 3 and 10 volts for different amounts of time (0, 30, 60 and 300 seconds). Evidence of 3'OH (deprotected) nucleotides in the samples was then assessed with LCMS and gel electrophoresis. Treated nucleotides were used for solution elongation of a primer by a mutant terminal deoxynucleotidyl transferase (SEQ ID NO: 1) that can couple 3'-hydroxyl nucleotides but not 3'-O-azidomethylnucleotides to the primer. The elongation reaction was as follows: 4 uM TdT, 136 uM dTTP (the treated nucleotides from microplate), 10 nmol primer (5'-FAM-polyTdU-3'-OH) with a reaction volume of 103 uL. After incubation for 10 min at 37° C. and removal of unincorporated monomers (1200 rpm), the products were separated by gel electrophoresis. LCMS showed evidence of deprotection by the appearance of a 3'OH dNTP band (not shown). The electropherogram of the separated products are shown in FIG. 8. The larger bands, clearly visible for the 300 sec samples (columns indicated by *), show that deprotected dTTP was in the treated samples and the azidomethyl group had been removed electrochemically, thereby permitting extension of the primers to form n+1 products.

Example 2

Electrochemical Control of 3'-O-Amino-Nucleotide Deprotection

Figure 9:
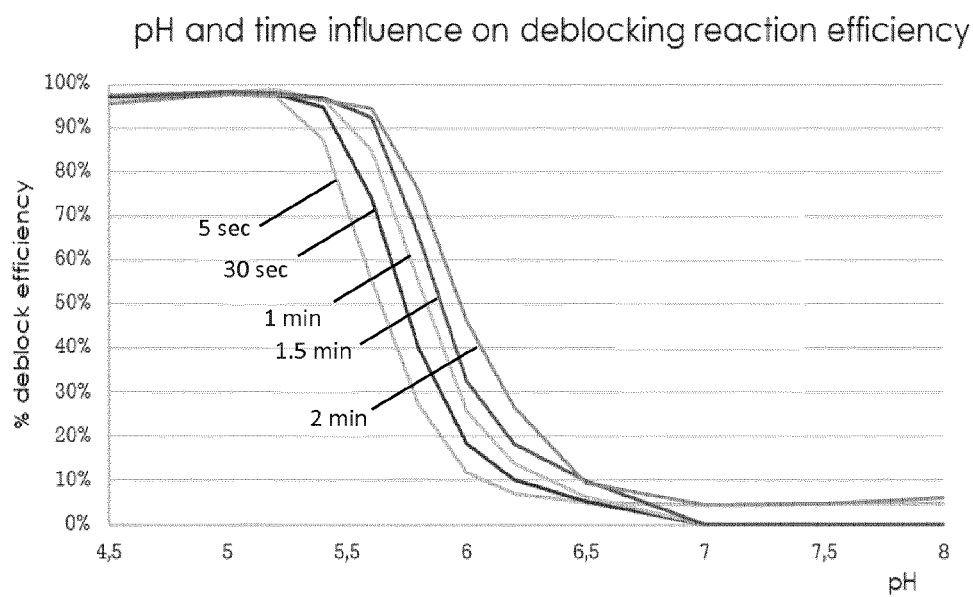
FIG. 9 illustrates efficiency of deprotecting 3'-O—NH2- nucleotides (that is, converting 3'-O—NH2 to 3'-OH) versus pH for several incubation times.

An aminoxy reversible protection group on a DNA's 3' end is cleaved by nitrosium ions (NO+) in acidic conditions, e.g. Benner, U.S. Pat. No. 7,544,794. In this experiment, pH of a deprotection buffer is electrochemically controlled via a quinone/hydroquinone redox system (e.g. Southern et al, U.S. patent publication US2004/0238369) to reduce locally pH from an initial value of 7.5 (yielding >0.5% deprotection after 2 minutes) to a final value of 5 (yielding >99% in less than 20 seconds). Results are illustrated in FIG. 9 where pH versus deprotection efficiency for several incubation times.

Definitions

"Microfluidics device" means an integrated system of one or more chambers, ports, and channels that are interconnected and in fluid communication and designed for carrying out an analytical reaction or process, either alone or in cooperation with an appliance or instrument that provides support functions, such as sample introduction, fluid and/or reagent driving means, temperature control, detection systems, data collection and/or integration systems, and the like. Microfluidics devices may further include valves, pumps, and specialized functional coatings on interior walls, e.g. to prevent adsorption of sample components or reactants, facilitate reagent movement by electroosmosis, or the like. Such devices are usually fabricated in or as a solid substrate, which may be glass, plastic, or other solid polymeric materials, and typically have a planar format for case of detecting and monitoring sample and reagent movement, especially via optical or electrochemical methods. Features of a microfluidic device usually have cross-sectional dimensions of less than a few hundred square micrometers and passages typically have capillary dimensions, e.g. having maximal cross-sectional dimensions of from about 500 μm to about 0.1 μm. Microfluidics devices typically have volume capacities in the range of from 1 μL to a few nL, e.g. 10-100 nL. The fabrication and operation of microfluidics devices are well-known in the art as exemplified by the following references that are incorporated by reference: Ramsey, U.S. Pat. Nos. 6,001,229; 5,858,195; 6,010,607; and 6,033,546; Soane et al, U.S. Pat. Nos. 5,126,022 and 6,054,034; Nelson et al, U.S. Pat. No. 6,613,525; Maher et al, U.S. Pat. No. 6,399,952; Ricco et al, International patent publication WO 02/24322; Bjornson et al, International patent publication WO 99/19717; Wilding et al, U.S. Pat. Nos. 5,587,128; 5,498,392; Sia et al, Electrophoresis, 24: 3563-3576 (2003); Unger et al, Science, 288: 113-116 (2000); Enzelberger et al, U.S. Pat. No. 6,960,437.

"Polynucleotide" or "oligonucleotide" are used interchangeably and each mean a linear polymer of nucleotide monomers or analogs thereof. Monomers making up polynucleotides and oligonucleotides are capable of specifically binding to a natural polynucleotide by way of a regular pattern of monomer-to-monomer interactions, such as Watson-Crick type of base pairing, base stacking, Hoogsteen or reverse Hoogsteen types of base pairing, or the like. Such monomers and their internucleosidic linkages may be naturally occurring or may be analogs thereof, e.g. naturally occurring or non-naturally occurring analogs. Non-naturally occurring analogs may include PNAs, phosphorothioate internucleosidic linkages, bases containing linking groups permitting the attachment of labels, such as fluorophores, or haptens, and the like. Whenever the use of an oligonucleotide or polynucleotide requires enzymatic processing, such as extension by a polymerase, ligation by a ligase, or the like, one of ordinary skill would understand that oligonucleotides or polynucleotides in those instances would not contain certain analogs of internucleosidic linkages, sugar moieties, or bases at any or some positions. Polynucleotides typically range in size from a few monomeric units, e.g. 5-40, when they are usually referred to as "oligonucleotides," to several thousand monomeric units. Whenever a polynucleotide or oligonucleotide is represented by a sequence of letters (upper or lower case), such as "ATGCCTG," it will be understood that the nucleotides are in 5'3' order from left to right and that "A" denotes deoxyadenosine, "C" denotes deoxycytidine, "G" denotes deoxyguanosine, and "T" denotes thymidine, "I" denotes deoxyinosine, "U" denotes uridine, unless otherwise indicated or obvious from context. Unless otherwise noted the terminology and atom numbering conventions will follow those disclosed in Strachan and Read, Human Molecular Genetics 2 (Wiley-Liss, New York, 1999). Usually polynucleotides comprise the four natural nucleosides (e.g. deoxyadenosine, deoxycytidine, deoxyguanosine, deoxythymidine for DNA or their ribose counterparts for RNA) linked by phosphodiester linkages; however, they may also comprise non-natural nucleotide analogs, e.g. including modified bases, sugars, or internucleosidic linkages. It is clear to those skilled in the art that where an enzyme has specific oligonucleotide or polynucleotide substrate requirements for activity, e.g. single stranded DNA, RNA/DNA duplex, or the like, then selection of appropriate composition for the oligonucleotide or polynucleotide substrates is well within the knowledge of one of ordinary skill, especially with guidance from treatises, such as Sambrook et al, Molecular Cloning, Second Edition (Cold Spring Harbor Laboratory, New York, 1989), and like references. Likewise, the oligonucleotide and polynucleotide may refer to either a single stranded form or a double stranded form (i.e. duplexes of an oligonucleotide or polynucleotide and its respective complement). It will be clear to one of ordinary skill which form or whether both forms are intended from the context of the terms usage.

"Primer" means an oligonucleotide, either natural or synthetic that is capable, upon forming a duplex with a polynucleotide template, of acting as a point of initiation of nucleic acid synthesis and being extended from its 3' end along the template so that an extended duplex is formed. Extension of a primer is usually carried out with a nucleic acid polymerase, such as a DNA or RNA polymerase. The sequence of nucleotides added in the extension process is determined by the sequence of the template polynucleotide. Usually primers are extended by a DNA polymerase. Primers usually have a length in the range of from 14 to 40 nucleotides, or in the range of from 18 to 36 nucleotides. Primers are employed in a variety of nucleic amplification reactions, for example, linear amplification reactions using a single primer, or polymerase chain reactions, employing two or more primers. Guidance for selecting the lengths and sequences of primers for particular applications is well known to those of ordinary skill in the art, as evidenced by the following references that are incorporated by reference: Dieffenbach, editor, PCR Primer: A Laboratory Manual, 2nd Edition (Cold Spring Harbor Press, New York, 2003).

"Sequence determination", "sequencing" or "determining a nucleotide sequence" in reference to polynucleotides includes determination of partial as well as full sequence information of the polynucleotide. That is, the terms include sequences of subsets of the full set of four natural nucleotides, A, C, G and T, such as, for example, a sequence of just A's and C's of a target polynucleotide. That is, the terms include the determination of the identities, ordering, and locations of one, two, three or all of the four types of nucleotides within a target polynucleotide. In some embodiments, the terms include the determination of the identities, ordering, and locations of two, three or all of the four types of nucleotides within a target polynucleotide. In some embodiments sequence determination may be accomplished by identifying the ordering and locations of a single type of nucleotide, e.g. cytosines, within the target polynucleotide "catcgc . . . " so that its sequence is represented as a binary code, e.g. "100101 . . . " representing "c-(not c)(not c)c-(not c)-c . . . " and the like. In some embodiments, the terms may also include subsequences of a target polynucleotide that serve as a fingerprint for the target polynucleotide; that is, subsequences that uniquely identify a target polynucleotide within a set of polynucleotides, e.g. all different RNA sequences expressed by a cell.

The invention claimed is:

1. A method of synthesizing a plurality of polynucleotides having predetermined sequences, the method comprising the steps of: (a) providing a spatially addressable array of reaction sites, wherein each reaction site is operationally associated with at least one working electrode and has disposed thereon initiators attached by their 5'-ends and having a 3'-O-electrochemically labile protecting group; (b) performing for each kind of nucleotide a cycle of (i) deprotecting initiators or elongated fragments at electrodes at predetermined addresses by generating a voltage difference between each of the electrodes at the predetermined addresses and a reference electrode so that the electrochemically labile protecting group is cleaved, thereby generating free 3'-hydroxyls on the initiators or elongated fragments at the electrodes of the predetermined addresses, (ii) contacting under elongation conditions the electrodes with a 3'-O-electrochemically labile-protected nucleoside triphosphate and a template-independent DNA polymerase so that the initiators or elongated fragments at the predetermined addresses are elongated by the incorporation of a 3'-electrochemically labile-protected nucleoside triphosphate to form 3'-O-electrochemically labile-protected elongated fragments; and (c) repeating step (b) until the array of polynucleotides of predetermined sequences is completed, wherein said electrochemically labile protecting group is an amino group and wherein said spatially addressable array of reaction sites is integrated in a semiconductor device.

2. The method of claim 1, wherein said voltage difference between said electrodes at said predetermined addresses and a reference electrode activates an electroactive agent at said predetermined addresses which changes the pH at said predetermined addresses, thereby cleaving said electrochemically labile protecting group.

3. The method of claim 1, wherein said template-independent DNA polymerase is a terminal deoxynucleotidyl transferase (TdT).

4. The method of claim 2, wherein said template-independent DNA polymerase is a terminal deoxynucleotidyl transferase (TdT).

5. The method of claim 1, wherein said semiconductor device is a Complementary Metal Oxide Semiconductor (CMOS) device.

6. The method of claim 5, wherein said template-independent DNA polymerase is a terminal deoxynucleotidyl transferase (TdT).

* * * * *